(12) United States Patent
Liang et al.

(10) Patent No.: US 6,936,470 B2
(45) Date of Patent: Aug. 30, 2005

(54) RAPID AND ENZYMELESS CLONING OF NUCLEIC ACID FRAGMENTS

(75) Inventors: Xiaowu Liang, La Jolla, CA (US); Andy Teng, Fullerton, CA (US); Shizhong Chen, San Diego, CA (US); Dongyuan Xia, Powell, OH (US); Philip L. Felgner, Rancho Sata Fe, CA (US)

(73) Assignee: Gene Therapy Systems, Inc., San Diego, CA (US)

(*) Notice: Subject to any disclaimer, the term of this patent is extended or adjusted under 35 U.S.C. 154(b) by 282 days.

(21) Appl. No.: 10/125,789

(22) Filed: Apr. 16, 2002

(65) Prior Publication Data

US 2003/0044820 A1 Mar. 6, 2003

Related U.S. Application Data

(63) Continuation of application No. 09/836,436, filed on Apr. 17, 2001.
(51) Int. Cl.[7] .................. C12N 15/63; C12N 15/85; C12N 15/87; C12N 15/00; C12N 15/09
(52) U.S. Cl. .................. 435/463; 435/455; 435/320.1
(58) Field of Search .................. 435/463, 455, 435/320.1, 464, 7

(56) References Cited

U.S. PATENT DOCUMENTS

| | | | |
|---|---|---|---|
| 4,897,355 | A | 1/1990 | Eppstein et al. |
| 4,965,188 | A | 10/1990 | Mullis et al. |
| 5,459,127 | A | 10/1995 | Felgner et al. |
| 5,561,053 | A | 10/1996 | Crowley |
| 5,612,180 | A | 3/1997 | Brown et al. |
| 5,621,080 | A | 4/1997 | Lin |
| 5,736,365 | A | 4/1998 | Walker et al. |
| 6,063,571 | A | 5/2000 | Uhlmann et al. |
| 6,063,604 | A | 5/2000 | Wick et al. |
| 6,165,720 | A | 12/2000 | Felgner et al. |
| 6,221,588 | B1 | 4/2001 | Bradshaw et al. |
| 6,280,977 | B1 | 8/2001 | Liang et al. |
| 6,509,156 | B1 | 1/2003 | Stewart et al. |

OTHER PUBLICATIONS

Zhang et al. A new logic for DNa engineering using recimbinaiton in *Escgerucgua coli* Nature Genetics vol. 20 1998.*
Cassata, Giuseppe, et al., "*Rapid expression of Caenorhabditis elegans homeobox open reading frames using a two–step polymerase chain reaction promoter gfp reporter construction technique*", Gene, An International Journal on Genes and Genomes, vol. 212, pp. 127–135 (1998).
Goodchild, John. "Conjugates of Oligonucleotides and Modified Oligonucleotides: A Review of Their Synthesis and Properties", Bioconjugate Chemistry, vol. 1, No. 3, pp. 166–187 (May/Jun. 1990).

Prodromou, Chrisostomos, et al., "*PROTOCOL, Recursive PCR: a novel technique for total gene synthesis*", Protein Engineering, vol. 5, No. 8, pp. 827–829 (1992).
Smith et al., "Genetic footprinting: A genomic strategy for determining a gene's function given its sequence," Proc. Natl. Acad. Sci. USA, 92: 6479–6483 (1995).
Vos et al., "AFLP: a new technique for DNA fingerprinting," Nucleic Acids Research, 23: 4407–4414 (1995).
Almarsson, et al. "Peptide Nucleic Acid (PNA) Conformation and Polymorphism in PNA–DNA and PNA–RNA Hybrids." Proc. Natl. Acad. Sci. USA, 90 9542–9546 (1993).
Benlin, et al. "Enhanced Peptide Nucleic Acid Binding to Supercoiled DNA Possible Implications for DNA "Breathing" Dynamics," Biochem., 35 8853–8859 (1996).
Bradshaw, et al. "A New Vector for Recombination–based Cloning of Large DNA Fragments from Yeast Artificial Chromosomes," Nucleic Acids Research, 23(23) 4850–4856 (1995).
Clark, J M. "Novel Non–templated Nucleotide Addition Reactions Catalyzed by Procaryotic and Eucaryolic DNA Polymerases," Nucleic Acids Research, 16(20) 9677–9686 (1988).
Demidov,et al. "Kinetics and Mechanism of Polyamide ("Peptide") Nucleic Acid Binding to Duplex DNA."Proc. Natl Acad Sci. USA, 92 2637–2641 (1995).
Demidov,et al. "Stability of Peptide Nucleic Acids in Human Serum and Cellular Extracts," Biochem Pharmacology, 48(6) 1310–1313 (1994).
Egholm, et al. "Efficient pH–Independent Sequence–Specific DNA Binding by Pseudoisocytosine–Containing bis–PNA," Nucleic Acids Research, 23(2) 217–222 (1995).
Egholm, et al. "PHA Hybridizes to Complementary Oligonucleotides Obeying the Watson–Crick Hydrogen–bonding Rules," Nature 365 566–568 (1993).
Egholm, et al. "Recognition of Guanine and Adenine in DNA by Cytosine and Thymine Containing Peptide Nucleic Acids (PNA)," J Am Chem. Soc. 114 9677–9678 (1992).

(Continued)

Primary Examiner—James Ketter
Assistant Examiner—Konstantina Katcheves

(57) ABSTRACT

A method for cloning a nucleic acid fragment into a vector by flanking the fragment with first and second adapter sequences, and contacting the fragment with the vector having sequences homologous to the first and second adapter sequences under conditions such that the nucleic acid fragment is incorporated into the vector by homologous recombination in vivo in a host cell. Additionally, a method for selecting for a successful transformation of a vector by a nucleic acid insert. Also, systems for cloning a nucleic acid fragment into a vector without at least one of a restriction enzyme, a ligase, a gyrase, a single stranded DNA binding protein, or other DNA modifying enzymes. Further, a kit for cloning a nucleic acid fragment into a vector.

86 Claims, 13 Drawing Sheets

OTHER PUBLICATIONS

Fakhfahk, et al. "Cell–free Cloning and Biolistic Inoculation of an infectious cDNA of Potato Virus Y," *J. of Gen. Virology*, 77 519–523 (1996).

Felgner, et al. "Nomenclature for Synthetic Gene Delivery Systems," *Human Gene Therapy*, 8 511–512 (1997).

Griffith, et al. "Single and Bis Peptide Nucleic Acids as Triplexing Agents Binding and Stoichiometry," *J. Am. Chem. Soc.* 117 831–832 (1995).

Higuchi, R. "Recombinant PCT," *PCR Protocols: A Guide to methods and Applications* New York Academic Press p 177–183 (1990).

Ido, et al. "Contruction of T–Tailed Vectors Derived from a pUC Plasmid a Rapid System for Direct Dloning of Unmodified PCR Products,"*Biosci. Biotech. Biochem.*, 61(10) 1766–1767 (1997).

Li, et al. "Delivery of a PCR Amplified DNA Fragment into Cells A Model for Using Synthetic Genes for Gene Therapy," *Gene Therapy*, 4 449–454 (19997).

Nielsen, et al, "Sequence–Selective Recognition of DNA by Strand Displacement with a Thymine–Substituted Polyamide," *Science*, 254 1497–1500 (1991).

Oliner, et al., "In vivo Cloning of PCR Products in *E. coli,*" *Nucleic Acids Research*, 21(22) 5192–5197 (1993).

Seed, B., "Purification of Genomic Sequences from Bacteriophage Libraries by Recombination and Selection in vivo," *Nucleic Acids Research*, 11(8) 2427–2445 (1983).

Sykes, et al., "Linear Expression Elements, A Rapid, in vivo. Method to Screen for Gene Functions," *Nature Biotechnology*, 17 355–359 (1999).

Zhang, et al., "A New Logic for DNA Engineering Using Recombination in *Eschenichia coli,*" *Nature Genetics*, 20 123–128 (1998).

Zhang, et al., "DNA Cloning by Homologous Recombination in *Eschenichia coli,*" *Nature Biotechnology*, 18 1314–1317 (2000).

* cited by examiner

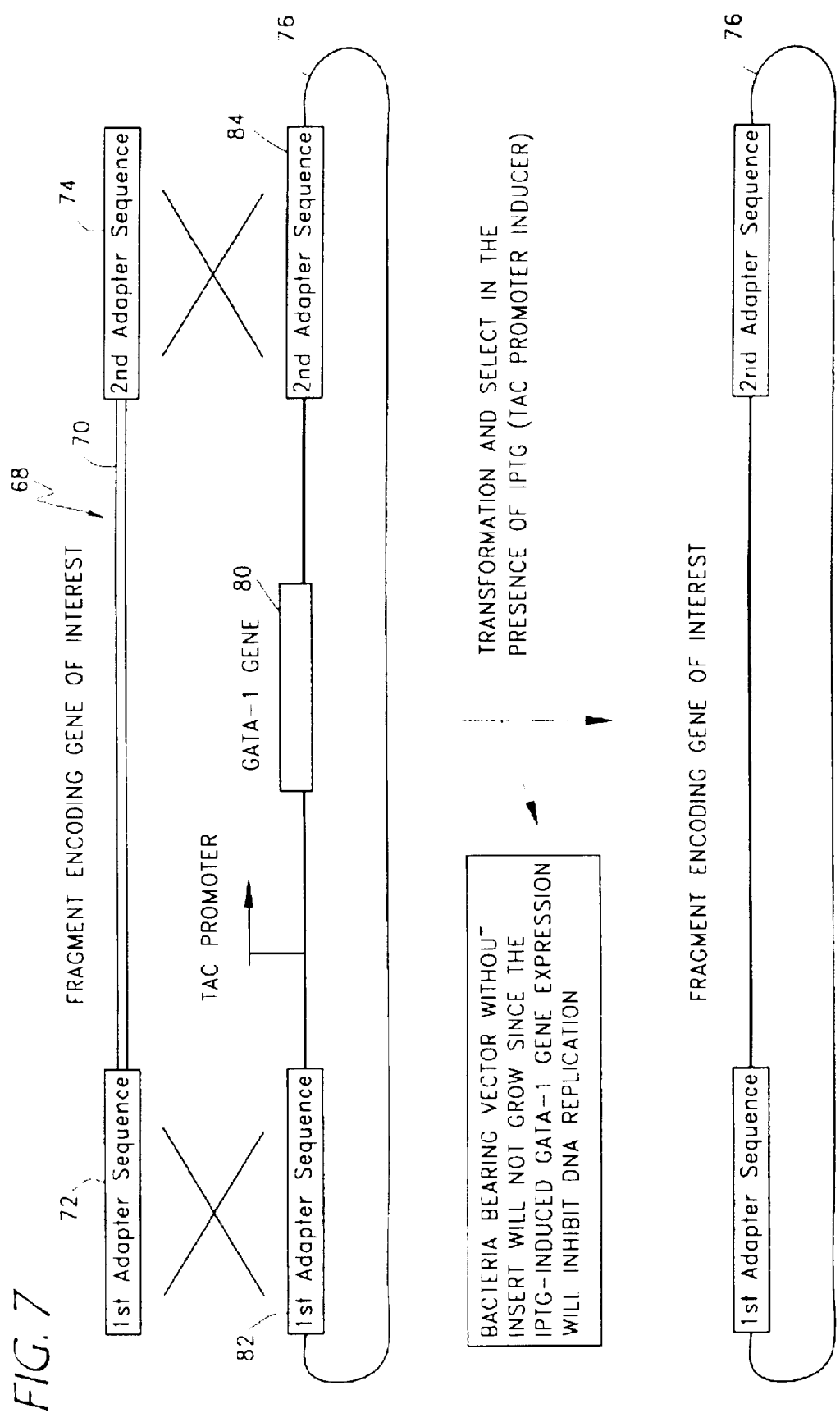

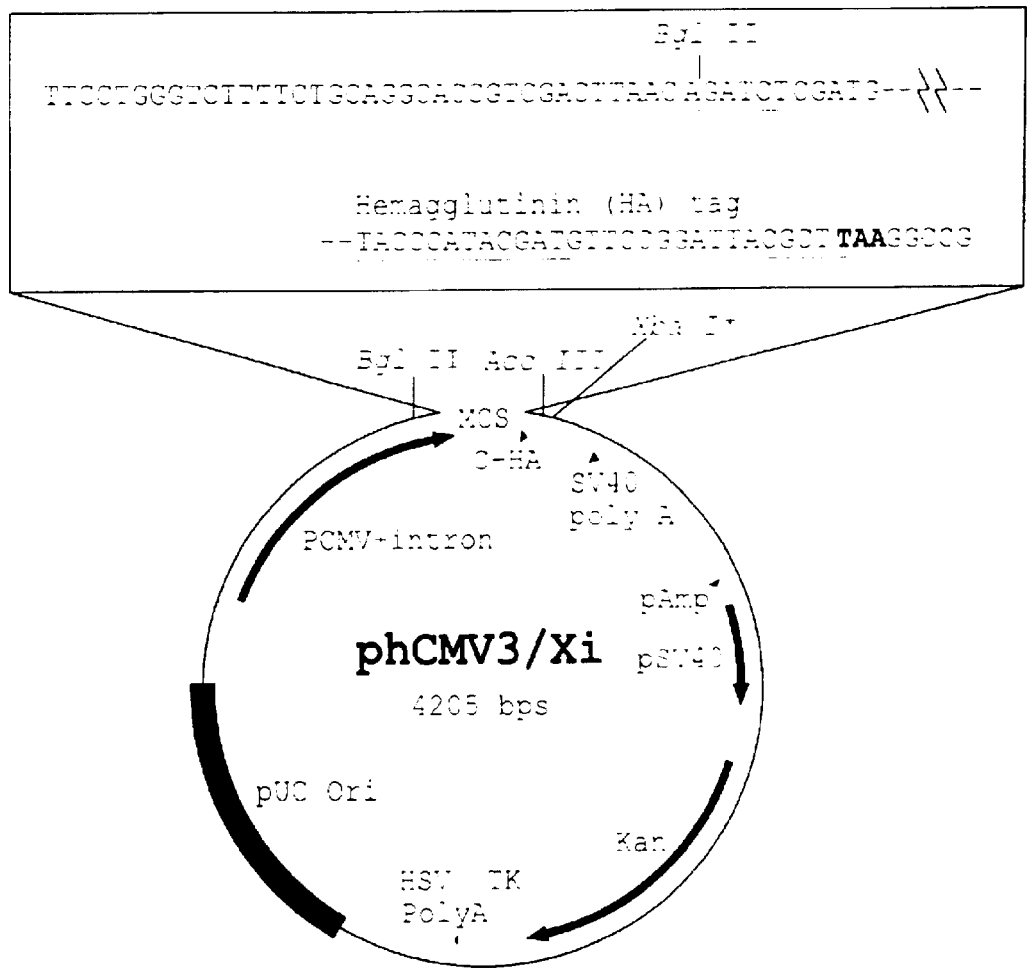

Vector Elements

| Element | Start-End | Description |
|---|---|---|
| C-HA | 1-27 | C-terminal Hemagglutinin tag sequence. |
| SV40 poly A | 181-231 | SV40 polyadenylation signal sequence |
| pAmp | 795-823 | Ampicillin resistance gene promoter sequence. |
| pSV40 | 907-1136 | SV40 promoter sequence. |
| Kan | 1258-2052 | Kanamycin resistance gene sequence. |
| HSV TK poly A | 2288-2306 | HSV Thymidine Kinase polyadenylation sequence. |
| pUC Ori | 2637-3280 | pUC origin of replication sequence. |
| pCMV+intron | 3421-4170 | Human CMV promoter/enhancer and intron sequence. |

RAPID AND ENZYMELESS CLONING OF NUCLEIC ACID FRAGMENTS

CROSS REFERENCE TO RELATED APPLICATIONS

This application is a continuation in part of U.S. application Ser. No. 09/836,436, filed on Apr. 17, 2001, entitled "FAST AND ENZYMELESS CLONING OF NUCLEIC ACID FRAGMENTS," which is hereby incorporated herein by reference in its entirety.

BACKGROUND OF THE INVENTION

1. Field of the Invention

The present invention relates to methods, systems and kits for fast and enzymeless cloning of nucleic acid fragments into vectors and for forced cloning selection for successful transformation.

2. Description of the Related Art

Traditional molecular cloning involves the use of recombinant DNA technology to propagate DNA fragments inside a foreign host. Generally, the DNA fragments are isolated from cDNA libraries or chromosomes and subcloned into a vector utilizing various enzymes. For example, a small amount (i.e., 0.01–0.03 µg) of isolated DNA fragment is contacted with a small amount (i.e., 0.01 µg) of linearized vector. Using enzymes, such as ligases, the fragments are ligated.

The DNA fragment-containing vector is introduced into a host cell according to various methods of transformation. For example, one tenth to one half of the ligation mix can be electroporated into a cell, such as $E.\ Coli$. Generally, a large number of cells, such as $1\times10^8$, is used to increase the ratio of cells to DNA fragment-containing vector to enhance the probability of obtaining a cell with the desired clone. For example, the ration might be 0.02–0.2 fg/cell.

A selection marker is usually included in the vector to increase the probability that the host cell has the DNA fragment-containing vector. Following introduction into the host cell and selection of the host cell containing the vector, the DNA fragment within the vector can then be replicated along with the host cell DNA. The DNA fragment-containing vector then can be isolated and purified from the host cell and transfected into animal cells or tissues for functional analysis of the encoded gene product.

Although the traditional enzymatic cloning methods have advantages such as pinpoint accuracy, they also have significant drawbacks. As mentioned, the methods require the use various enzymes that can be very expensive. In addition, the same DNA fragment has to be enzymatically treated every time it is introduced into a different vector. All of the vector may not be effectively cut by the enzymes, which can result in a higher number of background cells. Also, the methods involve slow and laborious processes. Selection of host cells containing the DNA fragment-containing vector entails significant labor and is still an uncertain process. Traditional cloning methods, even in conjunction with the use of polymerase chain reaction (PCR), are still time consuming, costly and difficult to automate.

The present invention provides simple and rapid methods, systems and kits for cloning nucleic acid fragments.

SUMMARY OF THE INVENTION

Embodiments of the present invention relate to methods for cloning a nucleic acid fragment into a vector by flanking the fragment with first and second adapter sequences. The fragment can be contacted with the vector having sequences homologous to the first and second adapter sequences under conditions such that the nucleic acid fragment is incorporated into the vector by recombination in a host cell. The first and second adapter sequences can be unique. The fragment can be directionally incorporated into the vector. The recombination can occur in vivo in the host cell.

The nucleic acid fragment can be generated by polymerase chain reaction (PCR). The first and second adapter sequences can be incorporated to the nucleic acid fragment by PCR. The resulting nucleic acid fragment can be a transcriptionally active PCR fragment.

The first and second adapter sequences further can include a functional element. The functional element can include, for example, a promoter, a terminator, a nucleic acid fragment encoding a selection marker gene, a nucleic acid fragment encoding a known protein, a fusion tag, a nucleic acid fragment encoding a portion of a selection marker gene, a nucleic acid fragment encoding a growth promoting protein, a nucleic acid fragment encoding a transcription factor, a nucleic acid fragment encoding an autofluorescent protein (e.g. GFP), and the like.

The nucleic acid fragment can include an additional element, such as, for example, an operably linked promoter, a termination sequence, an operon, a fusion tag, a signal peptide for intracellular or intercellular trafficking, a peptide, a protein, an antisense sequence, a ribozyme, a protein binding site, and the like.

The promoter can be, for example, a promoter from a plant or a plant pathogen, such as cauliflower mosaic virus, from a mammal or a mammalian pathogen, such as CMV, SV40, MMV, HIV, from a fungus, such as yeast (Gal 4 promoter), from a bacterium or a bacterial phage, for example, lambda, T3, T7, SP6 and the like. The terminator sequence can be derived from a plant, a procaryotyic source or a eukaryotic source, such as SV40, bovine growth hormone, rabbit beta-globin i, and the like. The operon can be, for example, lac operon, Tet/on operon, Tet/off operon, trp operon. The fusion tag can include 6× to 10× his-tag, GST tag, fluorescent protein tag, Flag tag, HA tag, and the like. The protein can include an enzyme, a receptor, a transcription factor, a lymphokine, a hormone, an antigen, and the like.

The vector can be, for example a plasmid, a cosmid, a bacterial artificial chromasome (BAC), and the like. The plasmid can be CoE1, PR100, R2, pACYC, and the like. The plasmid can be maintained in the host cell under the selection condition selecting for the functional selection marker. The vector can also include a functional selection marker, which for example can be a resistance gene for kanamycin, amplicillin, blasticidin, carbonicillin, tetracycline, chloramphenicol, and the like. The vector further can include a dysfunctional selection marker that lacks a critical element, and wherein the critical element is supplied by said nucleic acid fragment upon successful homologous recombination. The dysfunctional selection marker can be, for example, kenamycin resistance gene, kanamycin resistance gene, ampicillin resistance gene, blasticidin resistance gene, carbonicillin resistance gene, tetracycline resistance gene, chloramphenicol resistance gene, and the like. Further, the dysfunctional selection marker can be, for example, a reporter gene, such as the lacZ gene, and the like.

The vector can include a negative selection element detrimental to host cell growth. The negative selection element can be disabled by the nucleic acid fragment upon successful recombination. The negative selection element can be inducible. The negative selection element can be, for example, a mouse GATA-1 gene. The vector can include a dysfunctional selection marker and a negative selection element.

The host cell can be a bacterium. The bacterium can be capable of in vivo recombination. Examples of a bacterium include JC8679, TB1, DH5α, DH5, HB101, JM101, JM109, LE392, and the like.

The first and second adapter sequences can each be at least 11 bp, 15 bp, 20 bp, 25 bp, or 30 bp and the like. Further, the first and second adapter sequences can each be at least 35 bp, 40 bp, or 45 bp, and the like. Still further, the first and second adapter sequences can each be at least 50 bp, 60 bp, or greater than 60 bp, and the like.

The contacting can include transforming a host cell with the vector and the nucleic acid fragment. The transformation can include, for example, electroporation, more preferably chemical transformation, and the like.

In other embodiments, the host cell can be a bacterium bearing the vector. The bacterium can be capable of in vivo recombination. The bacterium can be, for example, JC8679, TB1, DH5α, DH5, HB101, JM101, JM109, LE392, and the like. The contacting of the vector and the nucleic acid fragment can include transforming the host cell bearing the vector with the nucleic acid fragment.

The vector that is borne in the host cell can be a plasmid. The plasmid can include a functional selection marker, such as, for example, a resistance gene for kanamycin, ampicillin, blasticidin, carbonicillin, tetracycline, chloramphenicol, and the like. The plasmid can include a dysfunctional selection marker that lacks a critical element, and wherein the critical element is supplied by said nucleic acid fragment upon successful recombination. The dysfunctional selection marker can be, for example a resistance gene for kanamycin, kenamycin, ampicilin, blasticidin, carbonicillin, tetracycline, chloramphenicol, and the like. Further, the dysfunctional selection marker can be, for example, a reporter gene, such as the lacZ gene, and the like.

Further, the vector borne in the host cell can include a negative selection element detrimental to host cell growth, and the negative selection element can be disabled by the nucleic acid fragment upon successful homologous recombination. The negative selection element can be inducible, for example. The negative selection element can be, for example GATA-1 gene. The vector can include a dysfunctional selection marker and a negative selection element.

The recombination can include for example, homologous recombination or any other like process. In some embodiments at least 65%, 70%, 75%, or 85% of the cells have undergone successful recombination. More preferably, 90% or 95% of the cells have undergone successful recombination. Still more preferably 96%, 97%, 98%, 99% or 100% of the cells have undergone successful recombination.

The vector can be a linearized vector, which can be prepared by the digestion of a vector and purification of digested vector. The purification can include chromatography and/or PCR. Also, the vector can be prepared by successive rounds of digestion.

The cell, the nucleic acid fragment(s) and the vector can be present at an amount of about $2 \times 10^7$, 0.4–2.0 µg, and 0.05–0.1 µg respectively, for example.

Other embodiments of the present invention relate to methods for selecting for successful transformation of a vector by a nucleic acid insert. The methods can provide a nucleic acid insert flanked by first and second adapter sequences that is adapted for recombining with homologous sequences in a vector. The vector can have a dysfunctional selection marker lacking a critical element and the nucleic acid insert contains the critical element. The nucleic acid insert can be contacted with the vector to effect recombination at homologous sites such that the critical element is supplied to the vector by the nucleic acid insert and the dysfunctional selection marker is restored to a functional one. The successfully restored selection marker can be selected for based upon growth of a host containing the successfully recombined vector that allows the host to grow or be identified in a selective environment. The recombining can be by recombination, such as for example, homologous recombination, and the like.

Further embodiments of the present invention relate to methods for selecting for successful transformation of a vector by a nucleic acid insert. The methods can include providing a nucleic acid insert flanked by first and second adapter sequences that is adapted for recombining with homologous sequences in a vector. The vector can include a negative selection element detrimental to cell growth. The nucleic acid insert can be contacted with the nucleic acid insert to effect recombination at homologous sites such that the negative selection element is disabled. Successful transformation can be selected for based on the absence of a functional negative selection element. The negative selection element can be inducible, for example. The selection step can include inducing the negative selection element. Methods utilizing the negative selection element further can include the methods for selecting for successful transformation of a vector by a nucleic acid insert, wherein the vector includes a dysfunctional selection marker lacking a critical element and the nucleic acid insert contains the critical element, as discussed above. The negative selection element can be disabled by insertion of a sequence encoding a selection marker.

Other embodiments of the present invention relate to systems for cloning a nucleic acid fragment into a vector without at least one of a restriction enzyme, a ligase, a gyrase, a topoisomerase, a single stranded DNA binding protein, or other DNA modifying enzymes. The system can include a nucleic acid fragment flanked by first and second adapter sequences and a vector having sequences homologous to the first and second adapter sequences wherein the nucleic acid fragment is adapted to incorporate into the vector by recombination. The recombination can include homologous recombination or any other like process. The nucleic acid fragment flanked by the first and the second adapter sequences can be generated by PCR without the use of at least one of a restriction enzyme, a ligase, a gyrase, a topoisomerase, a single stranded DNA binding protein, or any other DNA modifying enzyme. The nucleic acid fragment flanked by the first and the second adapter sequences can be a transcriptionally active PCR fragment.

Still further embodiments relate to systems for cloning a nucleic acid fragment into a bacterium without the use of at least one of a restriction enzyme, a ligase, a gyrase, a topoisomerase, a single stranded DNA binding protein, or any other DNA modifying enzyme. The system can include a nucleic acid fragment flanked by first and second adapter sequences and a bacterium bearing a vector, the vector having sequences homologous to the first and second adapter sequences, wherein the nucleic acid fragment is adapted to incorporate into the vector within the bacterium by recombination, such as for example, homologous recombination.

Embodiments also relate to kits for cloning a nucleic acid fragment into a vector. The kits can include reagents for amplification of the nucleic acid fragment or fragments, wherein the reagents upon amplification can provide for a nucleic acid fragment or fragments flanked by first and second adapter sequences; and can further include a vector, a competent cell, or a competent cell bearing the vector, and the like. The competent cell can be ready to be transformed by electroporation, chemical transformation, and the like. The competent cell or the competent cell bearing the vector can be a bacterium. The bacterium can be capable of in vivo recombination.

Further embodiments relate to methods of generating a substantially background-free linearized vector preparation. The methods can include providing a circular vector that includes a restriction enzyme cleavage site, wherein the site is flanked by homologous sequences; linearizing the vector with a restriction enzyme; and purifying the linearized vector to a purity. The purity can be substantially 98%, 99%, or 100%, for example, full length vector.

The purification can include chromatography, which can include for example, affinity chromatography. The affinity chromatography can include capturing an undigested vector, said undigested vector comprising a binding molecule in a cloning site such that the binding molecule is not present on the linearized vector due to cleavage by at least one restriction enzyme. The binding molecule can include a PNA binding sequence, for example. The affinity chromatography can include capturing only the linearized vector, where the linearized vector includes a binding site. For example, the binding site can include an end of the vector that is exposed by the restriction enzyme cleavage, wherein the end is captured by a complementary probe on the affinity column.

The purification also can include PCR amplification of the linearized vector. The purification can include PCR amplification of the linearized vector and chromatography purification. Further, multiple rounds of digestions can be included. The purification can result in substantially 98%, 99%, or 100% linearized vector composition, for example.

The linearizing step can include cleaving the vector at one site, two sites or more on the vector.

Still other embodiments relate to methods of introducing more than one nucleic acid fragment into a vector within a cell. The methods can include providing a first nucleic acid fragment that includes a first coding sequence flanked by a first and a second homologous sequence, wherein the first and second homologous sequences are added to the first coding sequence by PCR. The methods further can include providing a second nucleic acid fragment that can include a second coding sequence flanked by a third and a fourth homologous sequence, wherein the third and fourth homologous sequences are added to the second coding sequence by PCR. Further, the methods can include providing a linearized vector comprising a first end and a second end, wherein the first and second ends are respectively homologous to the first homologous sequence on the first nucleic acid fragment and to the third homologous sequence on the second nucleic acid fragment. Also, the methods can include introducing the nucleic acid fragments and the linearized vector into the cell under conditions such that the nucleic acid fragments are incorporated into the vector by recombination in the cell. The recombination can include homologous recombination or the like.

The methods can include culturing the recombinant cell. The methods can further include selecting a cell that has undergone successful recombination. The selecting can include growing the cell under selective conditions.

In some embodiments at least 50%, 60%, 65% or 70% of the cells have undergone successful recombination. Preferably, at least 75%, 80%, 85%, 90% of the cells have undergone successful recombination. More preferably, at least 95%, 99% or 100% of the cells have undergone successful recombination.

In some embodiments more than two nucleic acid fragments can be incorporated into a vector. For example 3, 4, 5, or more nucleic acid fragments can be designed. Each fragment will have appropriate homologous sequences to ensure directional incorporation into the vector.

The linearized vector can be prepared by the digestion of a vector and purification of the digested vector. The digestion can include cutting of the vector with a restriction enzyme. A vector can be prepared by PCR amplification so that digestion is not required. The purification can include chromatography. The purification can include PCR amplification of the linearized vector. The purification can result in a substantially 98%, 99%, 99.5%, or 100% linearized vector composition. The linearized vector of any of the embodiments of the invention can be prepared according to any of the methods described herein.

The first or said second homologous sequence can each include at least about 11, 15, 20, 21, 22, 23, 24, or 25 bases. Further each can include 30, 35, 40, 45, 50, or more bases, for example.

The introducing step can include chemical insertion of the nucleic acid fragments and the linearized vector into the cell. The chemical insertion can include co-introduction of the vector and the nucleic acid fragments. Any other introduction method can be used, such as electroporation, for example.

The cell, the nucleic acid fragments and the linearized vector can be present at an amount of about $2 \times 10^7$, 0.4–2.0 $\mu$g, and 0.05–0.1 $\mu$g respectively, for example.

Further embodiments relate to systems for cloning more than one nucleic acid fragment into a vector without at least one of a restriction enzyme, a ligase, a gyrase, a topoisomerase, a single stranded DNA binding protein or the like; the system can include more than one nucleic acid fragment each flanked by first and second adapter sequences, and a vector having sequences homologous to the adapter sequences on the 5' terminal nucleic acid fragment and the 3' terminal nucleic acid fragment, respectively, wherein the one or more nucleic acid fragment is adapted to incorporate into the vector by recombination.

Embodiments relate to kits for cloning at least one nucleic acid fragment into a vector comprising reagents for amplification of the nucleic acid fragment, wherein the reagents upon amplification provide for at least one nucleic acid fragment flanked by first and second adapter sequences, a vector, a competent cell, or a competent cell bearing the vector, and the competent cell is ready to be transformed by electroporation or chemical transformation.

Still other embodiments relate to methods of high throughput cloning that do not require colony selection. The embodiments described herein can be used in high throughput cloning because in some embodiments, little or no colony selection is required due to the high efficiency of cloning. The methods can include introducing a vector and one or more nucleic acid fragments designed to directionally recombine within a host cell, as described herein. The amount of cells, vector and fragment(s) can be those amounts discussed herein, for example. The cells are grown and no selection is necessary due to the high efficiency of recombination and cloning. For example, substantially 99%–100% of the cells have the correct vector and insert(s). Thus, cloning can be done rapidly in a high throughput manner. The cloned DNA can then be further utilized and/or manipulated as necessary. Thus, certain embodiments relate to methods for generating a plurality of recombinant constructs. The methods can include the steps of introducing into a host organism a linearized polynucleotide vector and a linearized polynucleotide vector insert, wherein the insert and the vector have respective regions of homology at ends thereof, under conditions favoring assembly of the vector and the insert into a circular recombinant construct in the host organism, such that such assembly occurs in at least about 95% of the host organisms; repeating the introducing step with the same or different vector and a different vector insert a plurality of times to produce a plurality of host organisms containing different recombinant constructs; and creating a collection of such host organisms by replicating the host organisms without a selection step. In some of the embodiments, assembly occurs in at least about 96, 97, 98, 99, or 100% of the host organisms.

The various specific features discussed above also can be used in the other embodiments discussed below and combined with each other in various combinations.

BRIEF DESCRIPTION OF THE DRAWINGS

FIG. 7 illustrates one embodiment relating to selection of a successfully transformed host.

FIG. 8 illustrates an exemplary vector, phCMV3/Xi.

DETAILED DESCRIPTION OF THE INVENTION

Figure 1:
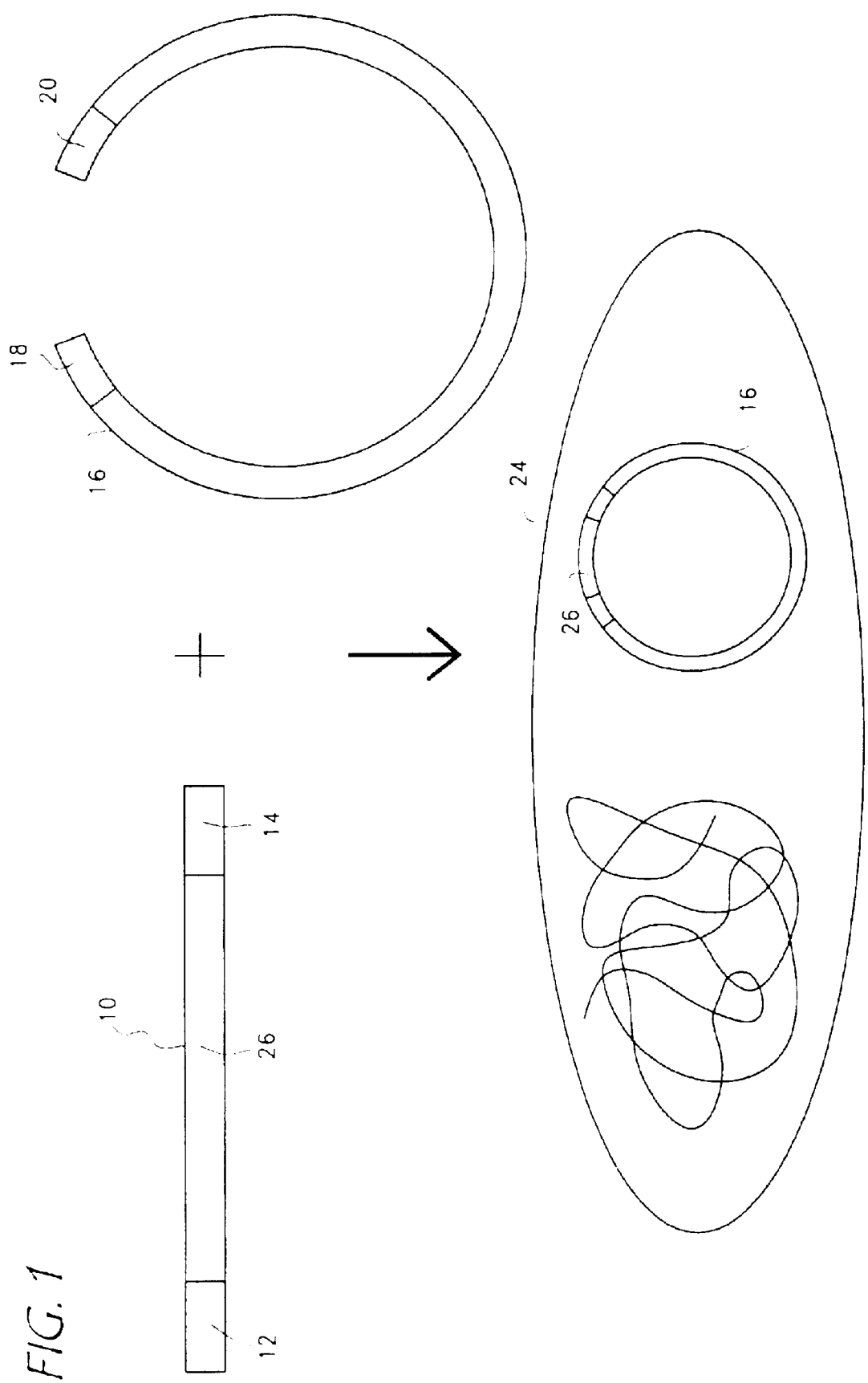
FIG. 1 depicts an embodiment of the present invention related to fast and enzymeless cloning into a vector.

The present invention, in at least certain embodiments, overcomes many of the above-described drawbacks of traditional cloning. The present invention includes methods, systems and kits for fast and simple molecular cloning of a nucleic acid fragment or more than one nucleic acid fragment directly into a vector without the use of enzymes, such as restriction endonuclease to cut the fragment(s), DNA ligase or any other DNA modifying enzyme. The invention includes methods for generating substantially background-free linearized vector. The present invention also includes simple and fast methods for selecting host cells containing the desired DNA fragment and vector.

The present invention generally provides methods, systems and kits for cloning a nucleic acid fragment into a vector by homologous recombination within a host cell. However, it should be noted that the present invention is not limited to one particular theory or mode of operation. It is not entirely clear, for example, that a homologous recombination mechanism will always be responsible for ligating the inserted fragment(s). Thus, the nucleic acid fragment may be cloned into a vector within a host cell by another intracellular mechanism besides or in addition to homologous recombination. For example, some other repair process in a cell may permit the fragment to be cloned into the vector as described herein. When the common sequences on both the 5' and 3' ends of the nucleic acid fragment are complimentary with terminal sequences in a linearized empty vector, and the fragment and linearized vector are introduced, by electroporation or more preferably by chemical transformation, for example, together into a host cell, they recombine resulting in a new expression vector with the fragment directionally inserted. In alternative embodiments the host cell can include the linearized empty vector so that only the nucleic acid fragment is introduced into the host cell. It should be noted that in alternative embodiments of the present invention the vector can be circularized, and as used herein a vector can be either linearized or circular. The host cell is converted into an expression vector through some mechanism within the host cell, such as for example, homologous recombination or some other repair or ligation process. In principle this approach can be applied generally as an alternative to conventional cloning methods.

One embodiment of the present invention includes a method for cloning a nucleic acid fragment flanked by first and second adapter sequences into a vector having homologous first and second adapter sequences. The nucleic acid fragment incorporates into the vector by recombination within a host cell. As used herein the term "recombination" is meant to broadly include any interaction that facilitates the incorporation of a nucleic acid fragment with a vector. The interaction can be in vivo or in vitro. Examples of recombination include homologous recombination, DNA repair mechanisms, and the like. Thus, in some embodiments the fragment or fragments may incorporate by homologous recombination or by some other intracellular mechanism.

More specifically, referring now to the embodiment of the present invention depicted in FIG. 1, a nucleic acid fragment 10 is flanked by a first adapter sequence 12 and a second adapter sequence 14. The nucleic acid fragment 10 also includes a coding region 26, which will be discussed more fully below. A vector 16 also has a first vector adapter sequence 18 and a second vector adapter sequence 20, which sequences are respectively homologous to the first and second adapter sequences 12, 14 of the nucleic acid fragment 10.

Figure 2:
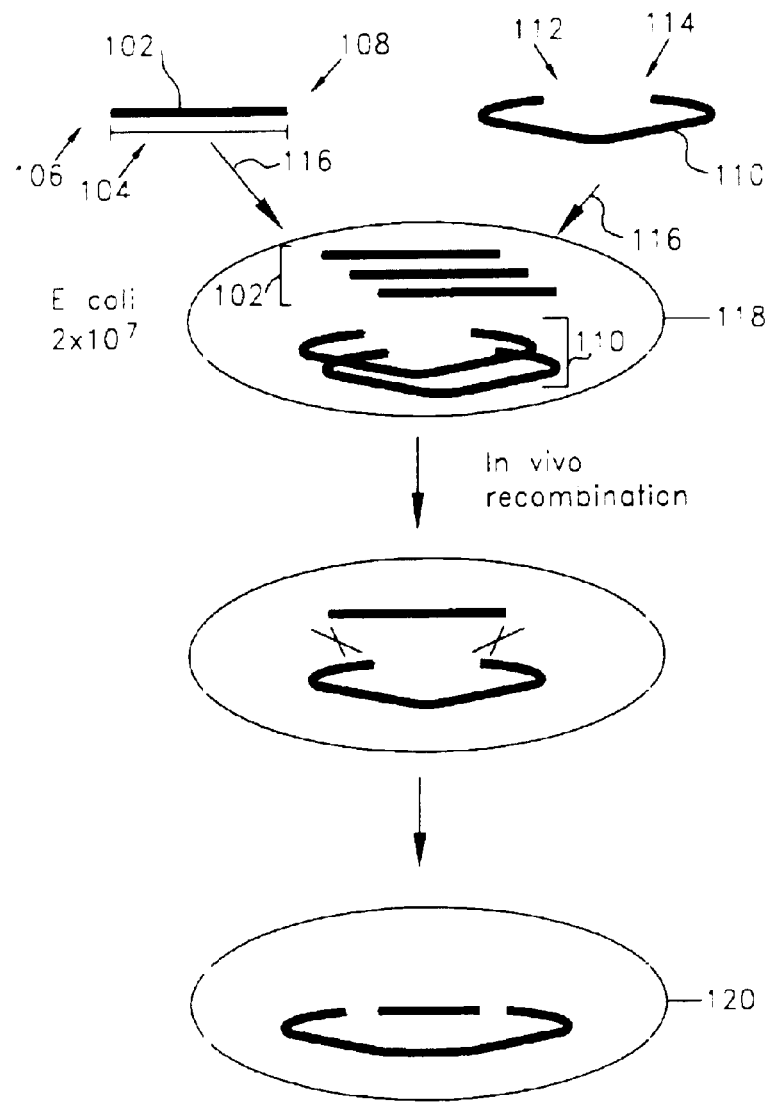
FIG. 2 illustrates one embodiment related to cloning a nucleic acid fragment into a vector.

FIG. 2 illustrates in further detail some of the embodiments of the invention. A nucleic acid fragment 102 includes a first adapter sequence 106 and a second adapter sequence 108, which flank a coding region 104. The nucleic acid fragment 102 also includes a coding region 104, which will be discussed more fully below. A vector 110 also includes a first vector adapter sequence 112 and a second vector adapter sequence 114, which sequences are respectively homologous to the first and second adapter sequences 106, 108 of the nucleic acid fragment 102.

The nucleic acid fragment 102 and the vector 110 are introduced 116 into a host cell 118, such as E. coli. Suitable cells are discussed more fully below. The introduction step 116 can include any method that permits a sufficient quantity of fragment 102 and vector 110 to be introduced into a host cell 118. Such methods are discussed more fully below. In preferred embodiments the introduction step includes chemical transformation, as discussed more fully below.

Once introduced into the cell, the nucleic acid fragment 102 incorporates 120 into or with the vector 118, for example by homologous recombination or any other process In some embodiments the ratio of nucleic acid fragment 102 and vector 110 to host cell 118 can be increased. This can permit a higher number of nucleic acid fragments 102 and vectors 110 to be introduced into an individual host cell 118. In some cases this may increase the frequency of inter-molecular reactions, such as in vivo homologous recombination or any other intracellular process or repair mechanism. Conversely, in some cases an increased number of host cells 118 in comparison to nucleic acid fragment 102 and/or vector 110 can result in a decrease in the frequency of incorporation of the nucleic acid fragment 102 with the vector 110. In preferred embodiments, the quantity of nucleic acid fragment 102 can be 0.4–2.0 μg and the quantity of vector 110 can be 0.05–0.1 μg. Further, in preferred embodiments that quantity of host cell 118 can be about $2 \times 10^7$ cells. In more preferred embodiments the ratio of total DNA molecules to host cell 118 can be about 20 fg to 100 fg per host cell.

Still further embodiments of the invention relate to methods, systems and kits for generating a protein fusion. More than one nucleic acid fragment can be cloned into a vector within a cell. For example, referring to FIG. 3, primers 130, 132 are designed, each with a sequence that is specific for a first coding region 134 and a sequence that adds an overlapping region 136, 138. PCR is performed and a first nucleic acid fragment 148 is generated, which includes the first coding region flanked by the overlapping regions 136, 138. The overlapping region 136 can be designed to be homologous to a first vector adapter sequence 154 on a vector 152. The overlapping region 138 can be designed to be homologous to an overlapping region 145 on a second nucleic acid fragment 150.

The second nucleic acid fragment 150 can be generated in a manner similar to the first nucleic acid fragment 148. Primers 140, 142 are designed, each with a sequence that is specific for a second coding region 144 and a sequence that adds an overlapping region 145, 146. PCR is performed and a second nucleic acid fragment 150 is generated, which includes the second coding region 144 flanked by the overlapping regions 145, 146. Overlapping region 146 can be designed to be homologous to a second vector adapter sequence 156 on vector 152. Overlapping region 145 can be designed to be homologous to overlapping region 138 on the first nucleic acid fragment 148.

The first nucleic acid fragment 148, the second nucleic acid fragment 150, and the vector 152 are introduced into a host cell (not shown). As discussed more fully below, the introduction can be accomplished by any appropriate method, such as for example, chemical transformation, electroporation, and the like. Also, as discussed more fully herein, any suitable host cell can be used.

Figure 3:
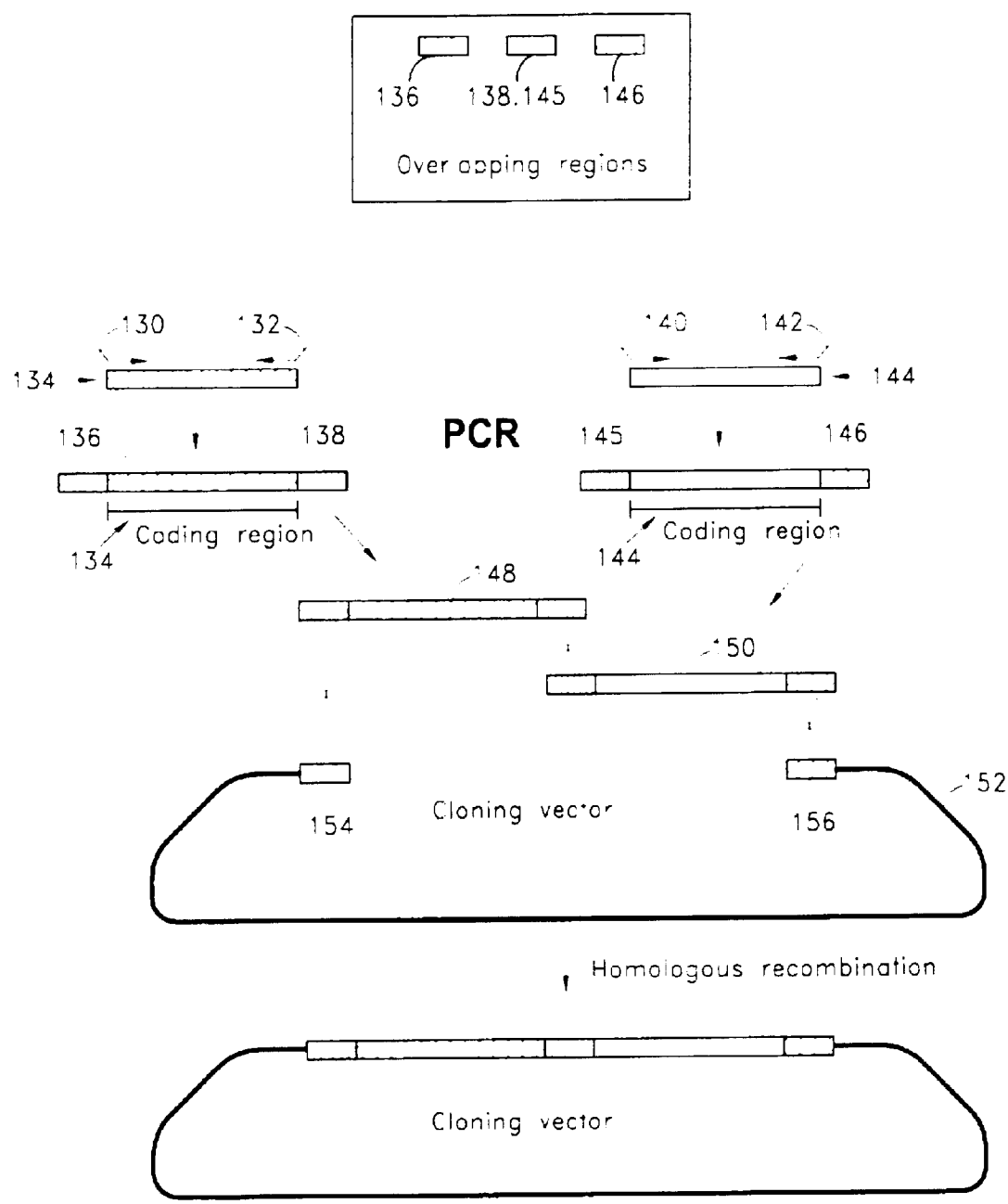
FIG. 3 illustrates an example of generating protein fusions.

Once introduced into the host cell, the first nucleic acid fragment 148 and the second nucleic acid fragment 150 incorporate with the vector 152 by a process. For example, the process can be homologous recombination, another cellular repair process, and the like. FIG. 3 illustrates an embodiment where two nucleic acid fragments are cloned into a vector.

Other embodiments of the invention relate to cloning more than two nucleic acid fragments into a vector. As described above, each successive nucleic acid fragment can be designed with an overlapping region that is homologous to an overlapping region on the next nucleic acid fragment.

Without being limited to any particular theory, presumably, once inside a host cell the homologous regions facilitate a recombination or repair process that causes the nucleic acid fragments to be joined and also to be incorporated into a vector.

In embodiments of the present invention the homologous first and second adapter sequences, the overlapping regions, or the homologous sequences of any of the embodiments can be at least 11 bp. In other embodiments the homologous first and second adapter sequences can be at least 15 or 20 bp. Further in embodiments the homologous first and second adapter sequences can be at least 25, 30 or 35 bp. The homologous first and second adapter sequences can be at least 40 bp. Also, the homologous first and second adapter sequences can be at least 50 bp. In preferred embodiments the homologous first and second adapter sequences are at least 60 bp. In more preferred embodiments the homologous first and second adapter sequences are at greater than 60 bp.

Certain embodiments of the invention relate to high efficiency cloning. For example, in some embodiments, regardless of the length of the adapter sequence or overlap region, a high percentage of host cells result that have the vector with nucleic acid fragment(s) incorporated into the vector. For the above-mentioned lengths, there can be an efficiency or percentage of cells with vector and correct nucleic acid fragment(s) insert of about 50%, more preferably, about 60% or about 70%, still more preferably, about 75% or about 85%. In more preferred embodiments the percentage of cells with the correct cloning vector and nucleic acid insert(s) can be about 90%, 91%, 92%, 93%, 94%, 95%, 96%, 97%, 98%, 99% or 100%, for example. As another example, in some embodiments, a homologous adapter sequence or overlap region of at least 20, 25, 30 or about 30 bp can result in 85% of the resulting cells having the vector with the nucleic acid fragment incorporated therein.

As mentioned above, the nucleic acid fragment of any of the embodiments of the invention can also include a coding region for a sequence or gene of interest. For example, a coding region is depicted in FIG. 1 as 26, in FIG. 2 as 104, and in FIG. 3 as 134 and 144. As used herein coding region refers generically to a region of a nucleic acid fragment that can encode, for example, an operably linked promoter, a termination sequence, an operon, a fusion tag, a signal peptide for intracellular or intercellular trafficking, a peptide, a protein, an antisense sequence, a ribozyme, a protein binding site, and the like.

In further embodiments, the coding region can encode any polypeptide or protein of interest. These can include enzymes, receptors, transcription factors, lymphokines, hormones, antigens, antibodies, fragments of any of the aforementioned, and the like. In some embodiments, the coding region can encode a polypeptide or protein of unknown function or portions of the same. In one embodiment the coding region can include a gene encoding a product which is absent or present at reduced levels in an organism. Nonlimiting examples of these gene products are the cystic fibrosis transmembrane regulator (CFTR), insulin, dystrophin, interleukin-2, interleukin-12, erythropoietin, gamma interferon, and granulocyte macrophage colony stimulating factor (GM-CSF). In some embodiments, the coding region can encode a functional motif or domain of a polypeptide or protein. These can include DNA binding domains, transcription activation domains, catalytic domains of kinases, phosphatases, and other enzymes or receptors, ligand binding domain of receptors, transmembrane domains of membrane-bound proteins or polypeptides, variable and constant domains of antibodies, protein-protein interacting domains, and the alike. As noted above, one of skill in the art need only know the terminal sequences of the coding region gene of interest in order to generate a nucleic acid fragment from a natural source or library comprising the gene with the first and second adapter sequences.

Figure 4:
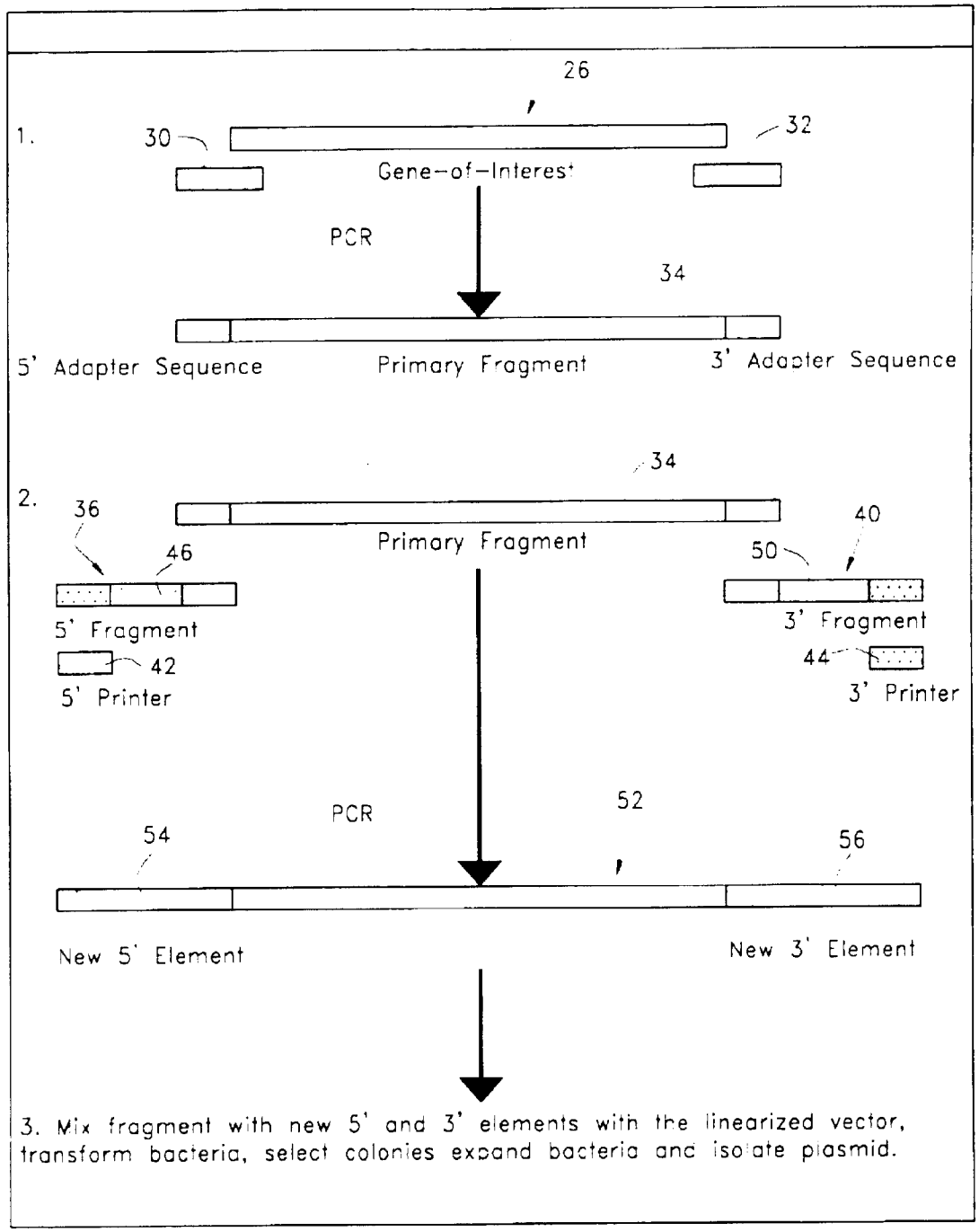
FIG. 4 illustrates one embodiment related to generating and cloning a nucleic acid fragment into a vector.

The nucleic acid fragment(s) with adapter or homologous regions can be generated by methods well known to those of skill in the art. Referring to the embodiment of the invention depicted in FIG. 4, a gene of interest 26 with known 5' and 3' sequences undergoes PCR along with overlapping 5' and 3' priming oligonucleotides 30, 32. The priming oligonucleotides can be obtained by methods known in the art, including manufacture by commercial suppliers. A primary fragment 34 with adapter sequences is generated. The adapter sequences flanking the gene of interest can be homologous to sequences on a vector, another primary fragment with adapter sequences, or to sequences from other 5' or 3' fragments to be used in a subsequent PCR, as will be discussed more fully below. The method depicted in FIG. 4 is more fully described in U.S. patent application Ser. No. 09/535,262, "Methods for Generating Transcriptionally Active DNA Fragments," which is hereby incorporated by reference in its entirety.

The nucleic acid fragment(s) from any other embodiment can also include a functional element. In some embodiments, an adapter sequence or overlapping region can include the functional element. In one embodiment the first and second adapter sequences, such as for example, 12, 14 of FIG. 1, can include the functional element. FIG. 4 illustrates one method for generating a nucleic acid fragment with functional elements. The primary fragment generated, as discussed above, has flanking sequences homologous to sequences on a 5' fragment 36 and a 3' fragment 40, respectively. The 5' and 3' fragments 36, 40 include functional elements 46 and 50, as well as a first and a second adapter sequence homologous to sequences on the primary fragment 34. A 5' primer 42 and 3' primer 44 for PCR can also be included. All undergo PCR. The resulting fragment 52 has a new 5' element 54 and a new 3' element 56 that include a functional element and terminal flanking sequences homologous to sequences on a vector. As noted above, the method is more fully described in U.S. patent application Ser. No. 09/535,262, "Methods for Generating Transcriptionally Active DNA Fragments," Liang, et al, which is hereby incorporated by reference in its entirety. For purposes of the present invention "transcriptionally active PCR fragment" or "transcriptionally active DNA fragment" refers to a nucleic acid fragment having a promoter and terminator sequence included therewith such that the fragment can be transcribed within a host cell. Depending upon the adapter sequences, the resulting vectors are useful for a variety of different applications.

One of skill in the art can readily configure orientations and generate nucleic acid fragments with such functional elements by methods well known in the art. In some embodiments, for example, the functional element can be a promoter, a terminator, a nucleic acid fragment encoding a selection marker gene, a nucleic acid fragment encoding a known protein, such as a fusion tag, a nucleic acid fragment encoding a portion of a selection marker gene, a nucleic acid fragment encoding a growth promoting protein, a nucleic acid fragment encoding a transcription factor, a nucleic acid fragment encoding an autofluorescent protein (e.g. GFP), and the like.

Nucleic acid fragments flanked by adapter sequences suitable for the purposes of the present invention can be generated using the TAP Express™ system (Gene Therapy Systems, San Diego, Calif.). The TAP Express™ uses nested PCR to append adapter sequences, which can include additional sequences such as a promoter and a terminator sequence, onto PCR fragments so that they become transcriptionally active and can be used directly in vitro and in vivo transfection experiments. The TAP Express™ system can be used to generate a large numbers of genes that can be conveniently amplified and introduced into functional assays in a single day, a task that is impractical or impossible using conventional cloning methodology.

As used herein, the term "promoter" is a DNA sequence which extends or is located upstream from the transcription initiation site and is involved in binding of RNA polymerase, or a DNA sequence which locates downstream from the transcription start site and is involved in binding of RNA polymerase III, and the like. The promoter may contain several short (<10 base pair) sequence elements that bind transcription factors, generally dispersed over >200 base pairs. A promoter that contains only elements recognized by general and upstream factors is usually transcribed in any cell type. Such promoters may be responsible for expression of cellular genes that are constitutively expressed (sometimes called housekeeping genes). There are also tissue-specific promoters limited to particular cell types, such as the human metallothionein (MT) promoter that is upregulated by heavy metal ions and glucocorticoids. The promoter can be selected based upon consideration of the desired use for the nucleic acid fragment. One skilled in the art easily can select an appropriate promoter according the uses of the nucleic acid fragment. For example, if the nucleic acid sequence encodes a gene with potential utility in human cells, then a promoter capable of promoting transcription in mammalian cells can be selected. Other examples of a promoter includes a promoter from a plant or a plant pathogen, such as cauliflower mosaic virus, and the like. The promoter can be from a mammal or a mammalian pathogen such as CMV, SV40, MMV, HIV, and the like. In other examples the promoter can be from a fungus such as a yeast (Gal 4 promoter), and the like, while in other examples it can be from bacteria or bacterial phage, for example lambda, T3, T7, SP6, and the like.

As used herein, the term "terminator" is a DNA sequence represented at the end of the transcript that causes RNA polymerase to terminate transcription. This occurs at a discrete site downstream of the mature 3' end, which is generated by cleavage and polyadenylation. For example, the terminator sequence can be derived from a plant, a procaryotyic or a eukaryotic source, such as SV40, bovine growth hormone, rabbit beta-globin i, and the like.

As used herein, the term "operon" is a controllable unit of transcription consisting of a number of structural genes transcribed together. An operon can contain at least two distinct regions, the operator and the promoter. Examples of operons include the lac operon, Tet/on operon, Tet/off operon, trp operon, and the like.

Term "fusion tag" is used herein to refer generally to a nucleic acid sequence encoding a molecule used to quantify, capture, purify, visualize, etc., the expressed protein to which the fusion tag is fused or attached. Examples of fusion tags include 6x or 8x his-tag, GST tag, fluorescent protein tag, Flag tag, HA tag, and the like.

It should be noted that in some embodiments, the vector can include a promoter, an operon, a terminator, a fusion tag, and the like. In such cases, the nucleic acid fragment may or may not include any of the same in addition to the vector.

In one embodiment the nucleic acid fragment(s) and the vector are introduced together into a host cell. Within the host cell the nucleic acid fragment incorporates into the vector by in vivo homologous recombination. The homologous sequence between the nucleic acid fragment and the vector can be recognized by the DNA recombination and repair mechanism (e.g., in *E. coli*) and joined together. In other embodiments, the incorporation can occur by any other reaction or process, such as another intracellular repair mechanism.

In another embodiment, the vector first can be mixed with the competent host cell. The host cell can be, for example, frozen away immediately. The competent host cell/vector mixture can be aliquotted and kept frozen. The transformation can be performed thawing the aliquot or using non frozen host cell, and adding only the desired nucleic acid fragment or PCR product to the host cell bearing the vector.

In another embodiment the nucleic acid fragment, can be introduced into the host cell bearing the vector. For example, the vector may be replicated with the host cell. Once the nucleic acid fragment is introduced into the host cell bearing the vector, it incorporates into the vector by in vivo by homologous recombination.

Figure 5:
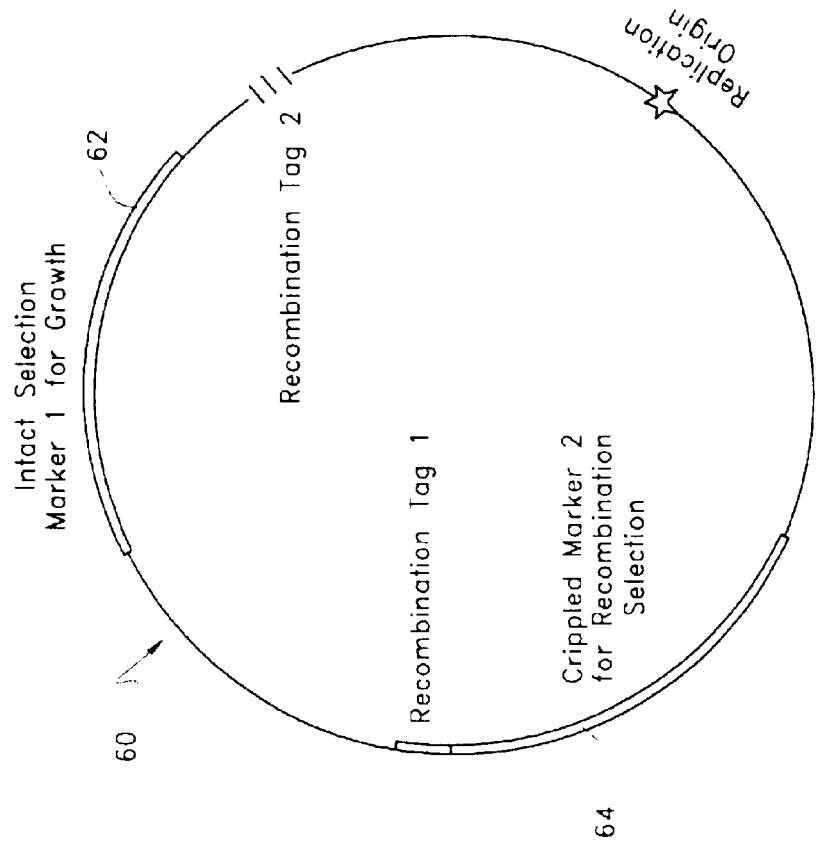
FIG. 5 depicts an exemplary receptor plasmid vector.

As used herein, the vector, including, for example, any vector described in FIGS. 1–3 can be a plasmid, a cosmid, a bacterial artificial chromasome (BAC), or the like. Examples of a plasmid include CoE1, PR100, R2, pACYC, and the like. FIG. 5 depicts one example of a plasmid that can be used in the present invention. The plasmid can include a functional or intact selection marker for growth. For example, FIG. 5 illustrates a plasmid vector 60 that includes an intact selection marker 62 for growth. Examples of a functional selection marker include a resistance gene for kanamycin, kenamycin, ampicillin, blasticidin, carbonicillin, tetracycline, chloramphenicol, and the like. The vector can be maintained in the host cell under the selection condition selecting for the functional selection marker. Other detailed examples of vectors are illustrated in FIGS. 8–13, including vectors suitable for mammalian expression.

In certain embodiments, the vector can be a linear vector. The vector can be linearized by any suitable method familiar to one of skill in the art. For example, a circular vector can be treated with at least one restriction endonuclease, or it may have a restriction site recognized by an endogenous endonuclease in the target organism/cell. In that case, the endonuclease cleaves the vector at a desired location thereby resulting in a linearized vector. The vector can be maintained in a linear state by any suitable method, including by maintaining the conditions of the medium to favor linearization. The linear vector can also be prepared by PCR using primers for that vector. The vector can be amplified using PCR.

Other embodiments of the invention relate to methods of generating substantially background free linearized vector. As used herein substantially-background free can mean a vector preparation that is at least about 80% linearized vector with the remaining portion being uncut or partially cut circular vector, for example. In other embodiments substantially-background free can mean at least about 85% linearized vector, more preferably, about 90% or 93% linearized vector. In still more preferred embodiments it can mean about 94%, 95%, 96%, 97%, 98%, or 99% linearized vector. In even more preferred embodiments, it can mean substantially 100% linearized vector. The term substantially 100% full length vector can mean that the purity of linearized vector is at least about 99.0 to 99.9% linearized vector. Linearized vector can be generated by providing a circular vector. The circular vector can have at least one restriction site. In preferred embodiments, the circular vector can have two or more restriction sites. The site or sites can be flanked by an adapter or homologous sequence that is homologous to sequence on the nucleic acid fragment that is to be inserted. The circular vector is cut at the at least one restriction site thereby causing it to be linearized. The linearized vector can be treated with phosphatase, such as calf intestine alkaline phosphatase, or DNA polymerase, such as T4 DNA polymerase, to prevent self ligation of the compatible sticky ends. The linearized vector can then be purified to a substantially background free purity, for example, or more preferably to a purity of substantially 100% full length vector.

The purification can be done by any suitable method by the skilled artisan. For example, the purification can include chromatography. The chromatography can be positive or negative chromatography, gel or other matrix chromatography, and the like. The digested vector can be captured. Alternatively, the undigested vector can be captured. One example of this is depicted in FIG. 5, which is discussed more fully below. The linearized vector can be captured. It can include a sticky end that will bind to a probe on a column, for example. The linearized vector can include a binding site that can be bound, for example. One of skill in the art will appreciate that any kind of chromatography can be designed and used.

Figure 6:
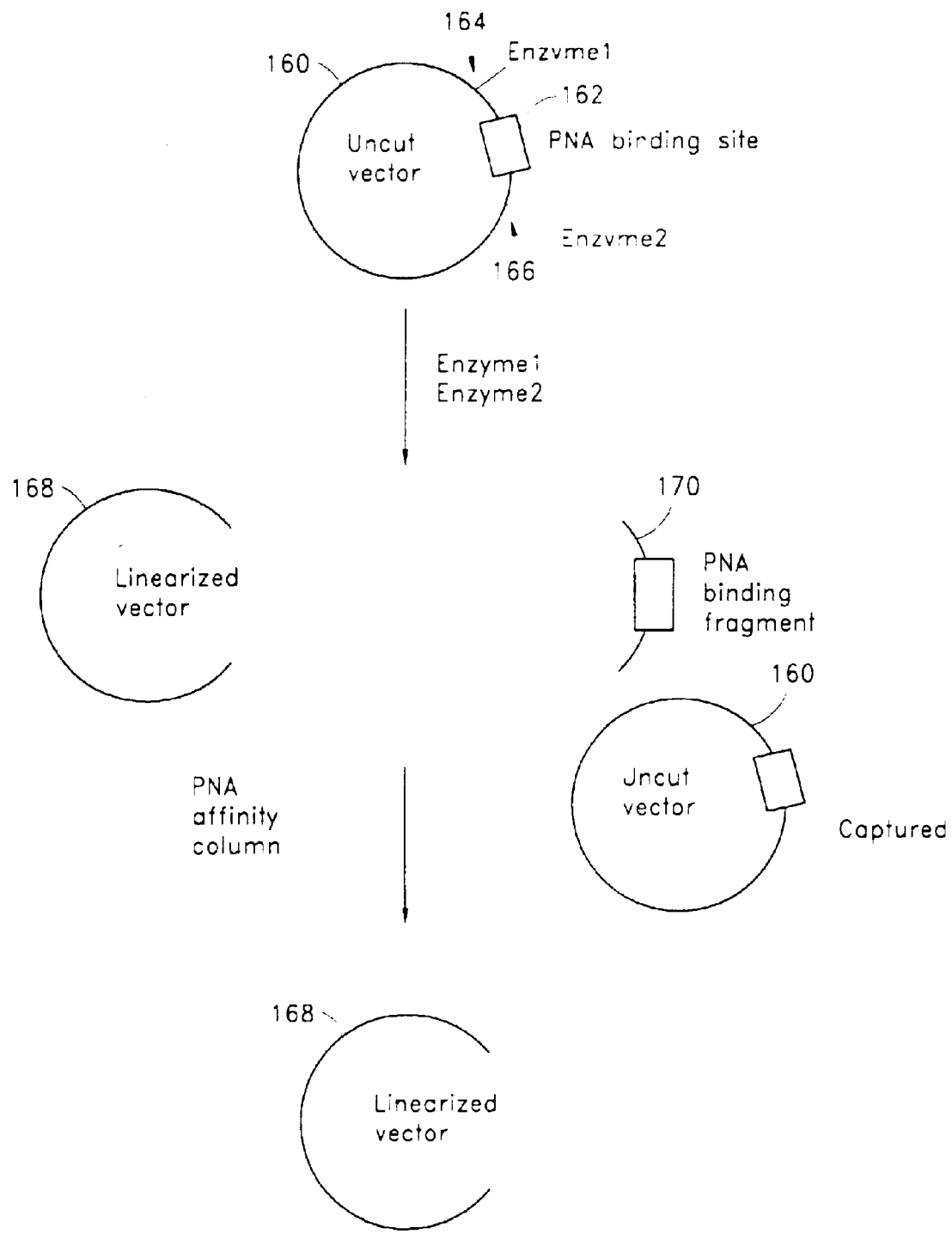
FIG. 6 illustrates one example of generating purified linearized vector.
Figure 9:
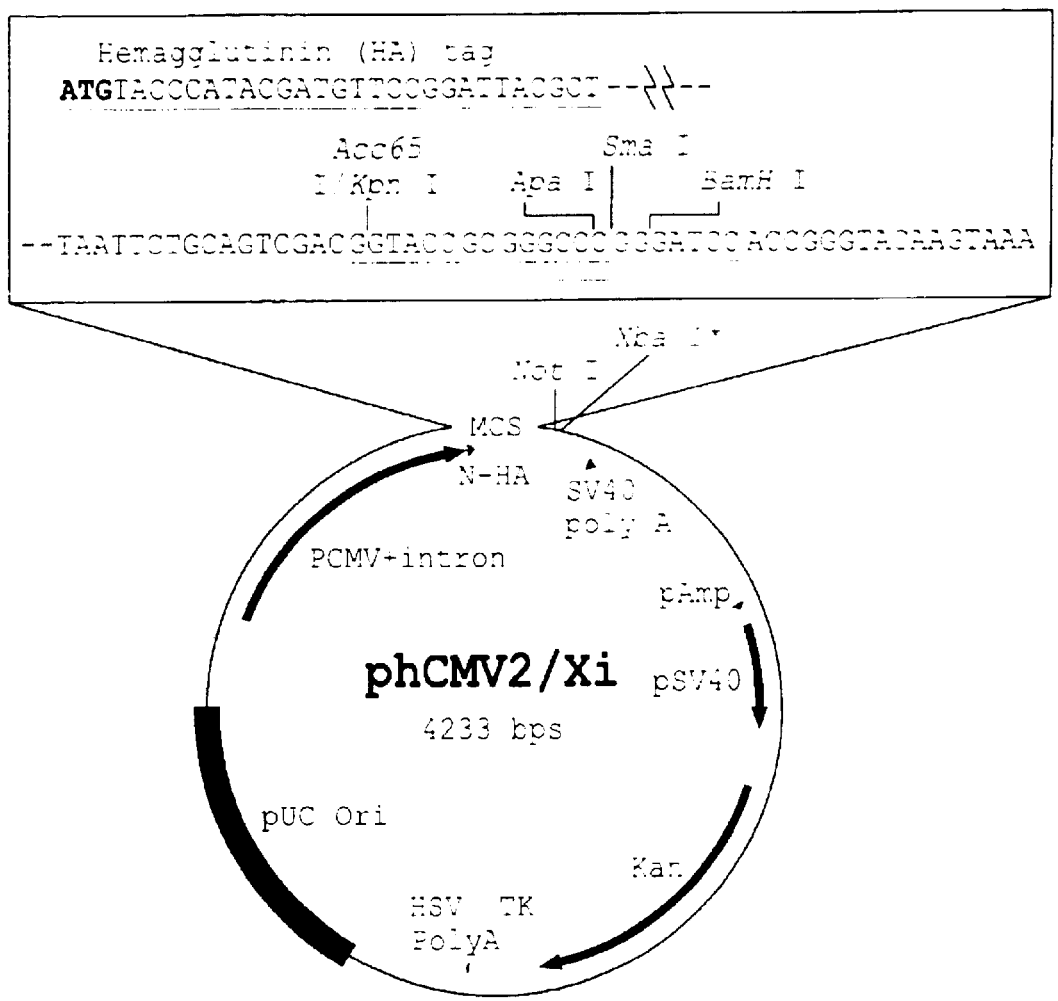
FIG. 9 illustrates an exemplary vector, phCMV2/Xi.
Figure 10:
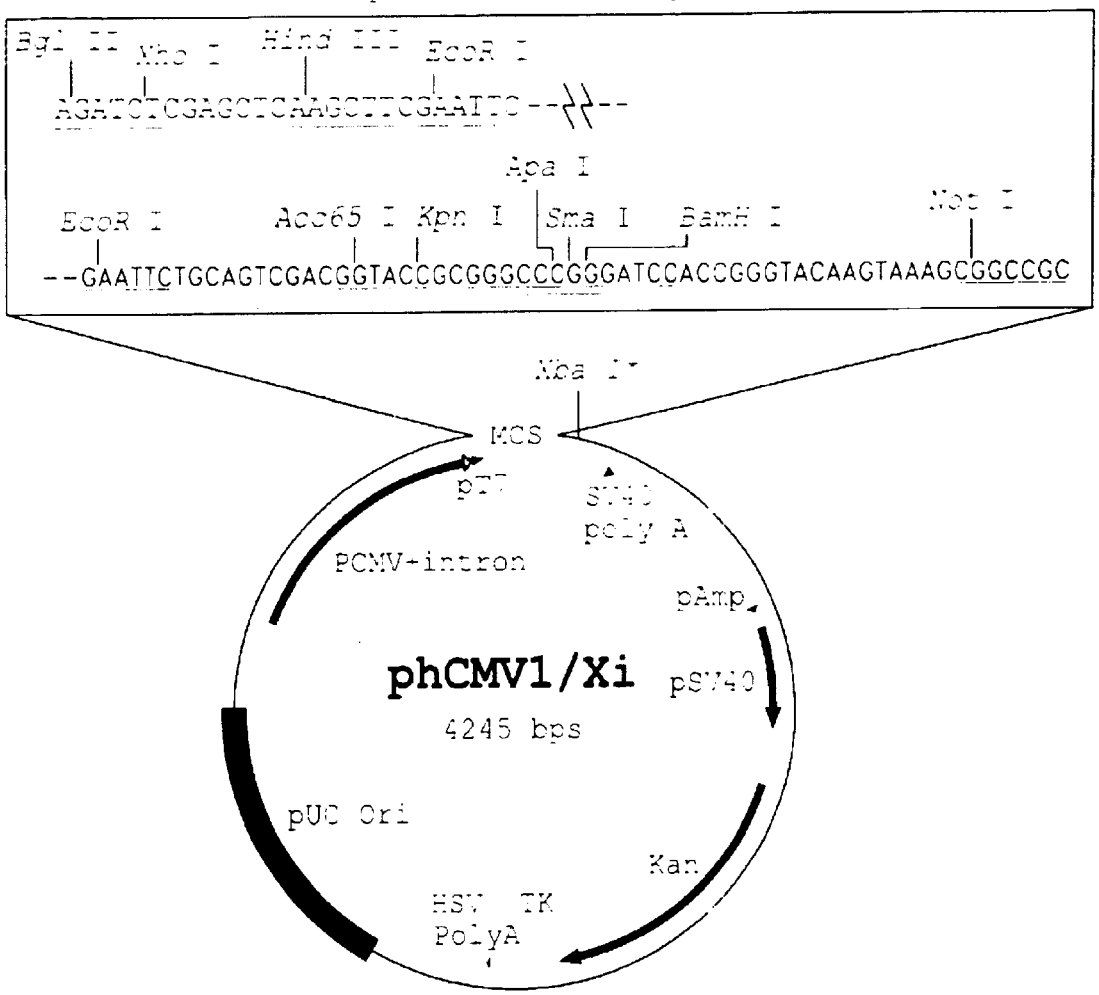
FIG. 10 illustrates an exemplary vector, phCMV1/Xi.
Figure 11:
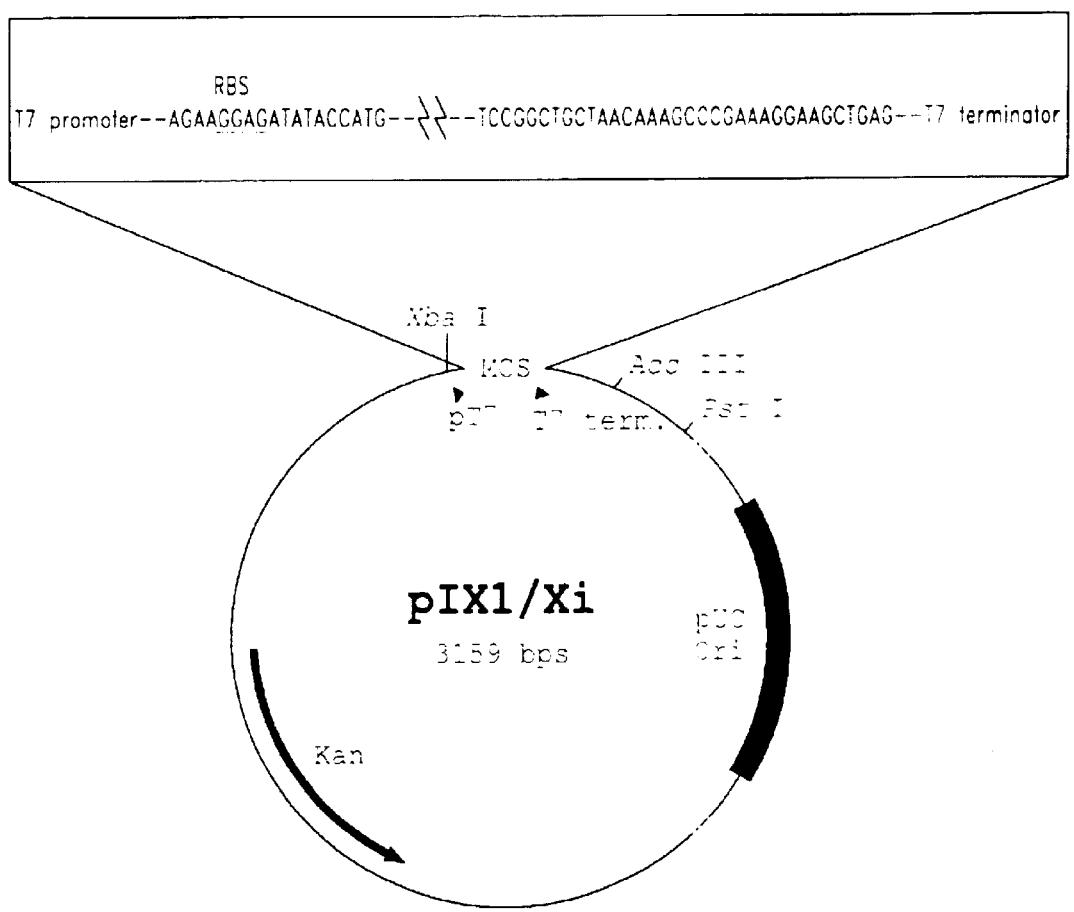
FIG. 11 illustrates an exemplary vector, pIX1/Xi.
Figure 12:
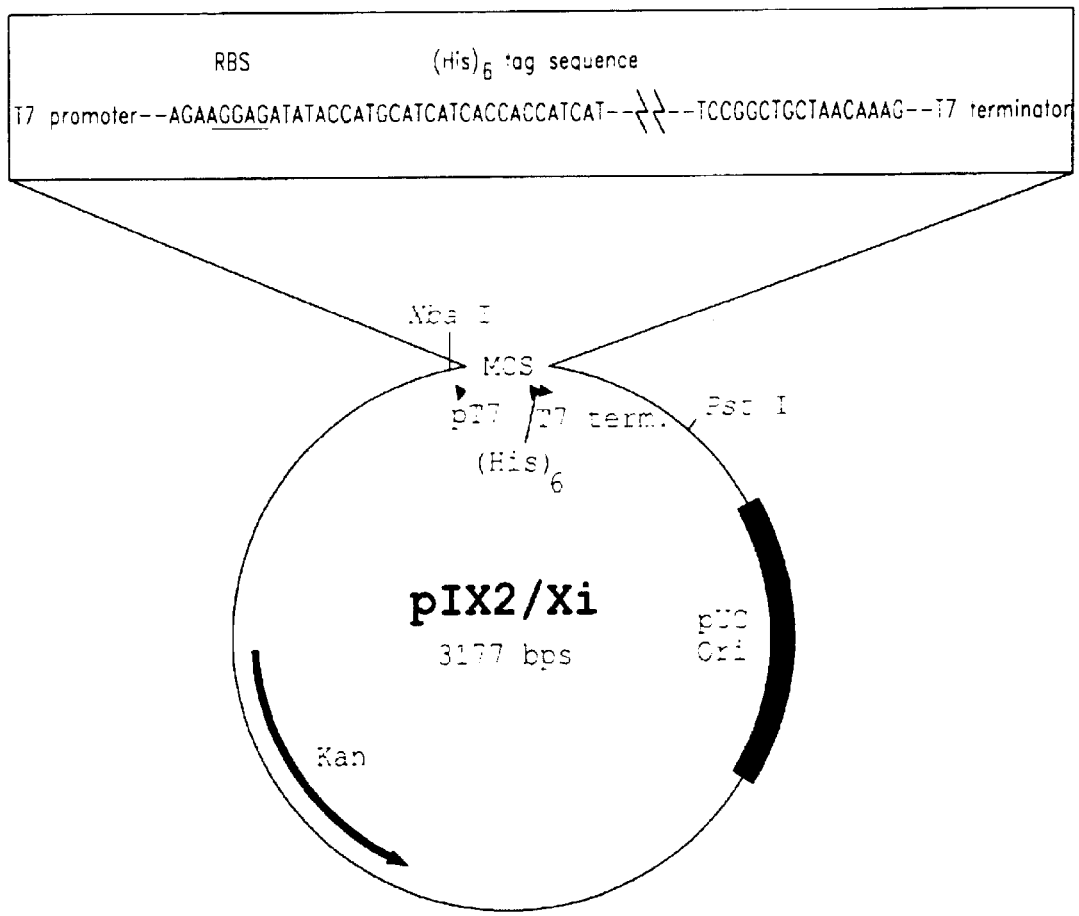
FIG. 12 illustrates an exemplary vector, pIX2/Xi.
Figure 13:
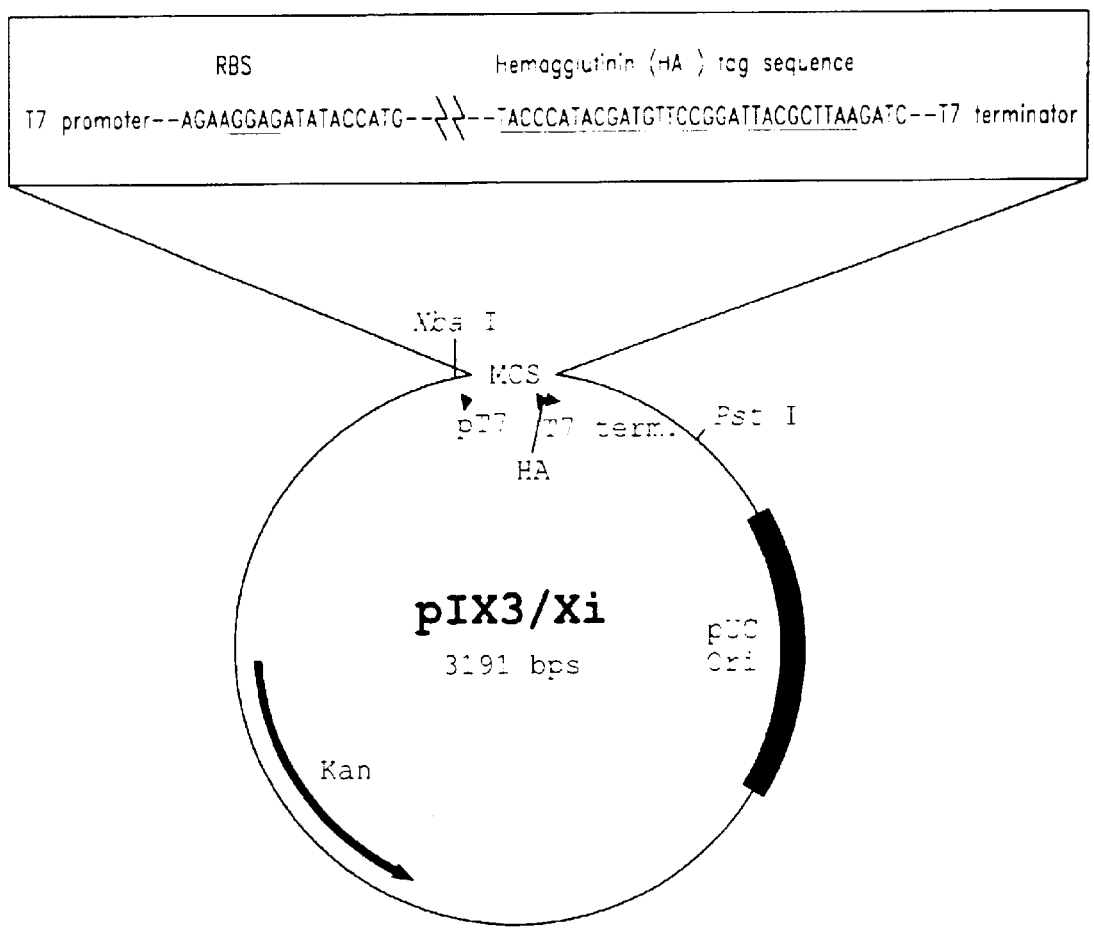
FIG. 13 illustrates an exemplary vector, pIX3/Xi.

Referring now to FIG. 6, uncut vector 160 includes a peptide nucleic acid (PNA) binding site 162 and restriction sites for enzyme 1 164 and enzyme 2 166. PNA binding sites and PNAs are well known in the art. For example, PNA binding and binding sites are disclosed in U.S. Pat. No. 6,280,977, issued on Aug. 28, 2001, and entitled METHOD FOR GENERATING TRANSCRIPTIONALLY ACTIVE DNA FRAGMENTS; and in U.S. Pat. No. 6,165,720, issued on Dec. 26, 2000, and entitled CHEMICAL MODIFICATION OF DNA USING PEPTIDE NUCLEIC ACID CONJUGATES; both of which are hereby incorporated by reference in their entirety. The vector is treated with enzyme 1 and enzyme 2 resulting in composition that includes linearized vector 168, PNA binding fragment 170 and uncut vector 160. The composition is run through a PNA affinity column. Uncut vector and PNA binding fragment 170 are captured by the column. Linearized vector 168 passes through and can be collected. Any steps of the process can be repeated.

The purification step can also include PCR amplification of the linearized vector. Each successive round of PCR can increase the amount of linearized vector. The PCR purification can be coupled with any of the other purification techniques, including the chromatography techniques.

Further, embodiments of the present invention include methods for selecting for successful transformation of a vector by a nucleic acid fragment. In one embodiment of the present invention the vector can include a dysfunctional selection marker that lacks a critical element. Upon successful in vivo homologous recombination, the lacked critical element is supplied to the vector by the nucleic acid fragment. As the homologous recombination and repair mechanism is not yet well characterized, it is of a relatively low frequency, making the identification of the intended recombined vector difficult. The inclusion of a critical element necessary for the viability of the host cell will facilitate selection of the intended vector, because only the correctly recombined vector can survive with the host, while a host only carrying either the insert or the vector alone cannot survive. This embodiment of the present invention can be referred to as "forced cloning." As an example, FIG. 5 illustrates a plasmid vector 60 having a dysfunctional or crippled marker 64 for recombination selection. Examples of a dysfunctional selection marker include an incomplete sequence of a resistance gene, for example kanamycin, kenamycin, ampicillin, blasticidin, carbonicillin, tetracycline, chloramphenicol, and the like. Additional examples include reporter genes, such as the lacZ gene, and the like. As used herein reporter gene refers to a gene that is used to locate or identify another gene. Other dysfunctional selection markers can include genes encoding products necessary for a metabolic or cellular pathway, and the like. One of skill in the art can easily select other useful "dysfunctional" selection markers based upon knowledge and skill common in the art.

The incomplete sequence, lacking a critical element, is completed by insertion of the lacked sequence or critical element upon a successful homologous recombination. In some embodiments the incomplete sequence can be missing at least a portion of a protein coding region, or, e.g., all or part of a regulatory element such as a promoter or termination sequence. The missing portion can be a major portion of the critical element or selection marker, or only a minor portion (e.g., one or more critical nucleotide residues).

A successfully transformed host can also be selecting for by a negative selection method. The vector can include a negative selection element. A negative selection element can be a sequence that encodes a molecule that is detrimental to growth of the host cell, such as, for example, the mouse GATA-1 gene product which is toxic to some cells. The toxic gene can be interrupted or replaced by a nucleic acid sequence that is correctly incorporated into the vector by homologous recombination. Only cells with a successfully incorporated "interrupting" sequence survive, because only those cells lack the toxic gene product. The negative selection element can also encode for molecules that block cell metabolism or prevent efficient transcription, and the like. One of skill in the art can easily select other elements that will work with the present invention.

In embodiments of the present invention the host cell can be a bacterium. In preferred embodiments the bacterium is capable of in vivo recombination. Examples of a bacterium include JC8679, TB1, DH5α, DH5, HB101, JM101, JM109, LE392, and the like. In some embodiments the bacterium may lack certain recombinase enzymes, such as RecT or RecE. For example, proper cloning has been observed in cells that typically are considered to be lacking in RecT, RecE or any other recombinase enzyme. This may be due, at least in part, to the favorable methods of the embodiments of the present invention. It may also be due, at least in part to, the presence of other repair or ligation mechanisms or other recombinases within the particular host cell.

In one embodiment the host cell can bear the vector. In preferred embodiments the host cell can be a bacterium. In more preferred embodiments the bacterium is capable of in vivo recombination. Examples of a bacterium that can bear the vector, as described above, can include JC8679, TB1, DH5α, DH5, HB101, JM101, JM109, LE392, and the like. In embodiments where the host cell bears the vector, only the nucleic acid fragment is introduced into the host cell, for example, by electroporation or chemical transformation.

As mentioned above, the nucleic acid fragment(s) and the vector can be introduced together into the host cell. Alternatively, the vector first can be introduced into the cell followed by a later introduction of the nucleic acid fragment(s) or simply the nucleic acid fragment(s) can be introduced into the host cell in order to transform the cell. In some embodiments relating to protein fusion, the vector and all of the nucleic acid fragments can be introduced together. Alternatively, the vector and fragments can be introduced individually by successive procedures, or combinations of vector and fragment(s) can be introduced followed by introduction of fragment(s). Further, the host cell can include a vector that replicates with the cell, thus obviating the need to introduce a vector into the host cell. In preferred embodiments the nucleic acid fragment(s) and/or vector can be introduced by electroporation, chemical transformation, and the like. In one preferred embodiment the nucleic acid fragment and the vector are introduced into an E. Coli cell by high efficiency electroporation. For example, in "high efficiency electroporation," as used herein, each microgram of a supercoiled plasmid, when delivered into a cell (such as E. Coli, for example) by electroporation, would be able to produce $10^{10}$ or more colonies. In more preferred embodiments, the vector and nucleic acid fragment(s) can be introduced by chemical methods. Such methods are well known in the art, and Example 8 below provides an exemplary method. For example, as mentioned above, the amount of insert can be about 0.4–2.0 μg. The amount of vector can be about 0.05–0.1 μg. The amount of E. coli cells can be about $2\times10^7$. Further, the ratio of total DNA to E. coli can be about 20–100 fg/cell.

In another embodiment the present invention also includes high efficiency electroporation-competent cells. Other preferred embodiments relate to chemically competent cells, such as E. coli, for example. These cells are capable of withstanding the conditions of chemical transformation, including the quantity of nucleic acid introduced into the cells. These cells significantly facilitate the introduction of insert and vector into the host cells, thus improving the efficiency of recombination, which is a bi-molecule reaction, that is exponentially dependent on the amount of substrate (the fragment and vector). Examples of these cells include JC8679, TB1, HB101, DH5α, DH5, JM101, JM109, and LE392 and the like.

As discussed briefly above, the present invention also includes methods and systems for forced cloning. Traditionally, a cloning vector will include a selection marker, such as a resistance gene, so that only a host cell having a properly incorporated DNA insert and vector will grow in a selective medium. However, the host cell may incorporate a vector having the resistance gene without the desired insert or with only a portion of the insert. Thus, host cell colonies will have to be screened, potentially at a significant time, material and labor cost, in order to identify a colony having the proper vector and insert.

Embodiments of the present invention relate to methods for selecting for the successful transformation of a vector by a nucleic acid insert. As an exemplary embodiment, referring to FIG. 1, the vector 16 is prepared with a dysfunctional selection marker that lacks a critical element. The nucleic acid fragment 10 can include the critical element. As used herein, the term "critical element" can refer to any sequence on the nucleic acid fragment 10 that, upon incorporation with the vector 16, restores functionality to a selection marker. For example, the critical element can be a promoter, a terminator, a nucleic acid fragment encoding a selection marker gene, a nucleic acid fragment encoding a known protein such as fusion tag, a nucleic acid fragment encoding a portion of a selection marker gene, a nucleic acid fragment encoding a growth promoting protein, a nucleic acid fragment encoding a transcription factor, a nucleic acid fragment encoding an autofluorescent protein (e.g. GFP), and the like. The resulting vector within the transformed host cell allows the host cell to grow in a selective medium. Thus, only host cells that are properly transformed with vector and nucleic acid fragment will grow. These embodiments minimize the need for subsequent, labor intensive and time consuming identification and selection of transformed cells.

In one embodiment, the vector can have a dysfunctional antibiotic resistance gene. For example, the vector can be prepared having an interrupted antibiotic resistance gene. The nucleic acid fragment is engineered to restore the functional antibiotic resistance gene upon incorporation into the vector by homologous recombination. The host cell having the "restored" vector can then be plated in a selective growth media. Any host cell lacking the "restored" vector will be unable to grow in the selective media.

In addition to the embodiments described above related to positive selection, embodiments of the present invention include methods, systems and kits relating to negative selection for a successful transformant. In one such embodiment, the vector can have a negative selection element that is detrimental to cell growth. For example, the negative selection element can be sequence that encodes a molecule that is toxic to the cell, a molecule that stops or prevents transcription, a molecule that is otherwise detrimental to growth of the host cell, and the like. When a nucleic acid fragment incorporates with the vector by homologous recombination within the host cell, the negative selection element is disabled. Disabling the negative selection element allows the host cell to grow, thus only cells with proper insertion of the nucleic acid fragment into the vector will survive and be selected.

The negative selection element can be inducible. For example, the vector can have a functional suicide gene or other negative selection element. The suicide gene can be replaced or disabled upon incorporation of the nucleic acid fragment into the vector by homologous recombination.

For example, referring to FIG. 7, a vector 76 can be prepared having a negative selection element 80, in this embodiment a mouse GATA-1 transcription factor gene. The negative selection element can be inserted between the first adapter sequence 82 and the second adapter sequence 84. The first and second adapter sequences 82, 84 have regions homologous to the ends of a nucleic acid fragment 68 that is to be cloned. The nucleic acid fragment 68 can be generated by PCR or any other suitable method, as discussed herein. The nucleic acid fragment 68 can encode some gene of interest 70 as discussed above. The fragment 68 includes a first adapter sequence 72 and a second adapter sequence 74, which are homologous to the first and second adapter sequences 82, 84 on the vector 76. The first and second adapter sequences 72, 74, as discussed above can also include additional elements, such as sequences encoding a promoter, a terminator, an operon, a fusion tag, and the like.

The negative selection element 80, in this case the GATA-1 gene, is under the control of TAC promoter inducible by IPTG, and its product is able to bind to the bacterial origin of replication, therefore resulting in a rapid arrest of cell growth. The nucleic acid fragment 68 upon incorporation into the vector 76 by homologous recombination will replace the negative selection element 80, thus enabling the host cell to grow in a selective media. Any host cells lacking the recombined vector will be unable to grow in the selective media.

The negative selection methods and systems can be combined with the other systems, methods, and kits, including for example, forced cloning. The nucleic acid insert can encode a critical element, as described above, that restores function to a disabled selection marker, while at the same time disabling a negative selection element, such as a suicide gene. Alternatively, the forced cloning methods, systems and kits can be used independently, in conjunction with the negative selection methods, systems and kits. In one embodiment, two nucleic acid fragments may be introduced into the host cell.

Another embodiment of the present invention relates to a system for cloning a nucleic acid fragment or fragments into a vector lacking at least one of the following: a restriction enzyme, a ligase, a gyrase, a single stranded DNA binding protein, or any other DNA modifying enzyme. The system can include a nucleic acid fragment flanked by first and second adapter sequences, and a vector having sequences homologous to the first and second adapter sequences. The nucleic acid fragment can be adapted to incorporate into the vector by homologous recombination or any other suitable process.

The nucleic acid fragment flanked by the first and the second adapter sequences can be generated by PCR without the use of a restriction enzyme, a ligase, a gyrase, a single stranded DNA binding protein, or any other DNA modifying enzyme as discussed above or according to any other method known in the art. The nucleic acid fragment flanked by the first and the second adapter sequences can be a transcriptionally active PCR fragment.

One embodiment of the present invention relates to a system for cloning a nucleic acid fragment or fragments, into a bacterium bearing a vector, without the use of a restriction enzyme, a ligase, a gyrase, a single stranded DNA binding protein, or any other DNA modifying enzyme. The system can include a nucleic acid fragment flanked by first and second adapter sequences and a bacterium bearing a vector having sequences homologous to the first and second adapter sequences. The nucleic acid fragment is adapted to incorporate into the vector within the bacterium by homologous recombination.

A further embodiment relates to a kit for cloning a nucleic acid fragment or fragments into a vector. The kit can include reagents for amplification of the nucleic acid fragment(s). Suitable reagents may include, for example, TAQ polymerase and/or PCR reagents such as adapter sequences capable of acting as primers for nested PCR and including regions of homology to a nucleic fragment of interest and regions added onto the ends of the nucleic acid fragment of interest upon successful amplification steps, as explained in more detail in U.S. Application Ser. No. 09/535,262, discussed above. The reagents upon amplification can provide for a nucleic acid fragment flanked by first and second adapter sequences, a vector, a competent cell, or a competent cell bearing the vector. The competent cell can form a part of the kit and can be ready to be transformed by electroporation, chemical transformation, or any like method known in the art. In preferred embodiments, the competent cell or the competent cell bearing the vector is bacteria. In other preferred embodiments the bacteria can be capable of in vivo recombination.

EXAMPLES

Example 1

Generation of Transcriptionally Active PCR Fragment Encoding Chloramphenicol Acetyltransferase (CAT)

The following components were combined in a 50 µl polymerase chain reaction (PCR): primers; 5'CTGCAG- GCACCGTCGTCGACTTAACAATG-
GAGAAAAAAATCACTGG3' (SEQ ID NO. 1); and
5'CATCAATGTATCTTATCATGTCTGATTACGC
CCCGCCCTGCCACTC3,'(SEQ ID NO. 2) 1 ng of DNA
template containing CAT coding region, 200 μM dNTP and
1 unit Taq DNA polymerase.

PCR was performed as follows: denaturation at 94° C. for
30 seconds, annealing for 45 seconds at 55° C. and extension
for 2 minutes at 72° C. for 25 cycles. The PCR product was
analyzed by electrophoresis in 1% agarose gel and purified
using a commercial PCR cleaning kit. A second PCR reaction was carried out using the product from the first PCR as
template. The reaction mix also contained 5 ng of DNA
fragment (800 bp) comprising a modified promoter sequence
from human cytomegalovirus (Gene Therapy Systems, San
Diego, Calif.), 5 ng of DNA fragment (200 bp) SV40
transcription terminator region, and 400 ng of primers
CMV154 and SV40-2. The PCR was performed under
similar conditions as above except the annealing temperature was raised to 60° C. and the extension time was
extended to 3 minutes. The resulting PCR product was
transcriptionally active and was used directly for transfection of cells in vitro or tissues in vivo.

Example 2

Cloning of Transcriptionally Active PCR Fragment
Encoding Chloramphenicol Acetyltransferase (CAT)

The PCR fragment of Example 1 was cloned by mixing
0.5 μg of the final PCR product with 0.1 μg of plasmid
pCMVm-SV40-T that was linearized and had sequences
identical to the sequences flanking the CAT gene in the PCR
fragment. The mixed PCR product and linear vector were
transformed into E. coli JC8679 through electroporation
followed by incubation in SOC medium at 37° C. for 1 hour
and plating on a LB/agar plate containing 100 μg/ml Kanamycin for selection over night at 37° C. Colonies were
selected and miniprep DNA was isolated for further analysis
and insertion of the PCR product into the vector.

Example 3

Cloning of PCR Fragment Encoding
Chloramphenicol Acetyltransferase (CAT) Using
Chemically Competent Cells The $1^{st}$ PCR fragment of Example 1 was cloned by
mixing 0.5 μg of the final PCR product with 0.1 μg of
plasmid pCMVm-SV40-T that was linearized and had
sequences identical to the sequences flanking the CAT gene
in the PCR fragment. The mixed PCR product and linear
vector were transformed into $10^7$ E. coli DH5α chemically
competent cells on ice for 15 minutes followed by incubation in SOC medium at 37° C. for 1 hour and plating on a
LB/agar plate containing 100 μg/ml Kanamycin for selection
over night at 37° C. Colonies were selected and miniprep
DNA was isolated for further analysis and insertion of the
PCR product into the vector.

Example 4

Vector Linearization

The pXic-His vector was linearized by Bam H1 restriction
enzyme digestion at 37° C. over night (8 units/1 ug DNA).
After digestion the sticky-ends generated by the restriction
enzyme were filled in with Taq DNA polymerase, Super-
Mix (Invitrogen, CA), at 72° C. for 15 minutes. The linearized vector was also dephosphorylated with alkaline phosphatase (calf intestinal alkaline phosphatase, CIP;
Invitrogen, CA) to eliminate re-circularization of the vector
by self-ligation. The linearized vectors were cleaned with
the PCR cleaning kit (Qiagen) and stored at 0.05 ug/ul in TE
buffer. Although there was no obvious indication of uncut
vector based on the agarose gel, after the above treatment
uncut vector was still apparent based on the presence of a
high frequency of colonies lacking the insert (40% of the
colonies lacked insert). The uncut vector was reduced by
doing a second round of restriction digestion as described
above. The background of the "double cut" vector was only
25%.

Example 5

Generation of Linear Vector By PCR

The background transformation of the uncut vector also
can be limited by using a "PCR vector". The PCR vector was
generated with two primers that matched to the ends of the
linearized vector. The PCR was done with the manufacturer's PCR protocol and proof-reading enzyme, pfx, from
Invitrogen. After PCR production and cleaning, the PCR
vector was stored in TE buffer at 0.05 ug/ul. This vector was
used in place of the linearized vector as describe in Example
4. A no background recombination cloning was obtained
with this "PCR vector." This 100% efficiency cloning technique can be used for high throughput cloning.

Example 6

Forced Cloning Using a Suicide Gene

A plasmid is constructed in such that the toxic gene
GATA-1 is under the control of tac (IPTG-inducible) promoter. The GATA-1-expressing unit is then flanked by TAP
promoter (modified CMV IE promoter/intron, 800 bp) and
TAP terminator (SV40 transcription terminator, 200 bp)
sequences. A Transcriptionally active PCR fragment encoding CAT gene is generated using the same promoter and
terminator elements. 2 μg of such TAP fragments is transformed into competent bacteria cells that contains the
GATA-1/TAC plasmid and prepared in the absence of IPTG.
After transformation, bacteria are plated on a LB plate
containing 10 ng/ml IPTG. Only the cells bearing the
plasmid in which the TAC/ATA-1 is replaced by the TAP
fragment encoding gene of interest are able to grow.

Example 7

Linearized Vector Purification

Uncut vector creates background colonies that contain
uncut vector without insert. Affinity chromatography can be
utilized to remove uncut vector. A PNA binding sequence is
inserted into the poly linker site of the vector and this
sequence is excised when the vector is linearized. In other
words, only the uncut vectors have the PNA binding site and
are able to bind the PNA affinity column. The cut out sites
containing the PNA binding site may also be captured by the
column. The linearized vector lacking the PNA binding site
will not bind to the column. After restriction enzyme
digestion, the product is loaded to the PNA affinity column
and the linearized vector collected from the follow through,
thus eliminating the uncut vector from the cut vector (see
FIG. 5 as an example). This procedure can generate a vector
leading to up to 100% efficiency, i.e. zero background, for
example.

Example 8

Six different circular vectors were linearized using the
materials as specified in Table 1, below. A portion of the
linearized vectors was treated a second time to further
linearize the vectors using the materials as specified in Table
2, below.

TABLE 1

| Plasmid | Linearize Vectors for Cloning | | | | 50 ug in 1 ml | | | after fill-in and clean (by PCR) | | |
| --- | --- | --- | --- | --- | --- | --- | --- | --- | --- | --- |
| | size | plasmid # | WFI | Buffer | BSA | plasmid | 37 C. cut AM | O/N 37 C. cut PM | Final Conc (ug/ul) | Final Vol (ul) | ID |
| phCMV Clone | | | | | | | | | | | |
| pST | 4236 bp | p0031 | 820 ul | 100 ul EcoRI Buffer | 10 ul | 30.1 ul 1.66 ug/ul | EcoRI 20 ul | EcoRI 20 ul | 0.1 | 500 | #1 |
| pST-nHA | 4261 bp | p0032 | 779 ul | 100 ul EcoRI Buffer | 10 ul | 31.3 ul 1.6 ug/ul | NheI 20 ul EcoRI 20 ul | NheI 20 ul EcoRI 20 ul | 0.1 | 500 | #2 |
| pST-cHA | 4248 bp | p0033 | 781 ul | 100 ul BamHI buffer | 10 ul | 29.2 ul 1.71 ug/ul | XhoI 20 ul BamHI 20 ul | XhoI 20 ul BamHI 20 ul | 0.1 | 500 | #3 |
| for pIX Clone | | | | | | | | | | | |
| pXIC | 3236 bp | p0041 | 768 ul | 100 ul BamHI buffer | 10 ul | 42.4 ul 1.18 ug/ul | NcoI 20 ul BamHI 20 ul | NcoI 20 ul BamHI 20 ul | 0.1 | 500 | #4 |
| pXIC-nHis | 3180 bp | p0042 | 780 ul | 100 ul BamHI buffer | 10 ul | 70 ul 0.71 ug/ul | BamHI 20 ul | BamHI 20 ul | 0.1 | 500 | #5 |
| pXIC-cHA | 3271 bp | p0043 | 643 ul | 100 ul BamHI buffer | 10 ul | 167 ul 0.3 ug/ul | NcoI 20 ul BamHI 20 ul | NcoI 20 ul BamHI 20 ul | 0.1 | 500 | #6 |

Note:
pST        1.66 ug/ul (mega)    EcoRI    20 units/ul    EcoRI buffer
pST-nHA    1.6 ug/ul (mega)     NheI     10 units/ul    Buffer 2
pST-cHA    1.71 ug/ul (mega)    BamHI    20 units/ul    BamHI buffer
pXIC       1.18 ug/ul (mega)    NcoI     10 units/ul    Buffer 4
pXIC-nHis  0.71 ug/ul (maxi)    XhoI     20 units/ul    Buffer 2
pXIC-cHA   0.3 ug/ul (maxi)

Verify the cut completion by gel (load 5 ul, i.e. 0.25 ug)
Store the cut plasmid at −20 C. or proceed to next step.
(2) Fill-in
Add 100 ul Supermix to the cut plasmid 1 ml
Incubate at 72 C. for 15 min to fill-in.
(3) Clean
Clean the cut plasmid using Qiagen PCR cleaning kit    (10 ug/kit, 5 kits per plasmid)
Elute with 100 ul WFI per kit.
Combine all 5 kits (~500 ul, ~0.1 mg/ml).
Run gel (load 2.5 ul, ~0.25 ug) to verify DNA conc.

TABLE 2

| Plasmid | Repeat Linearize Vectors for Cloning | | | | 50 ug in 1 ml | | | after Qiagen PCR clean kit | | |
| --- | --- | --- | --- | --- | --- | --- | --- | --- | --- | --- |
| | size | plasmid # | WFI | Buffer | BSA | plasmid* | 37 C. cut PM | O/N 37 C. cut AM | Final Conc (ug/ul) | Final Vol (ul) | ID |
| phCMV Clone | | | | | | | | | | | |
| pST | 4236 bp | p0031 | 350 ul | 100 ul EcoRI Buffer | 10 ul | 500 ul 0.1 ug/ul | EcoRI 20 ul | EcoRI 20 ul | 0.1 | 500 | #1 |
| pST-nHA | 4261 bp | p0032 | 310 ul | 100 ul EcoRI Buffer | 10 ul | 500 ul 0.1 ug/ul 20 ul | NheI 20 ul EcoRI 20 ul | NheI 20 ul EcoRI | 0.1 | 500 | #2 |
| pST-cHA | 4248 bp | p0033 | 310 ul | 100 ul BamHI buffer | 10 ul | 500 ul 0.1 ug/ul | XhoI 20 ul BamHI 20 ul | XhoI 20 ul BamHI 20 ul | 0.1 | 500 | #3 |
| for pIX Clone | | | | | | | | | | | |
| pXIC | 3236 bp | p0041 | 310 ul | 100 ul BamHi buffer | 10 ul | 500 ul 0.1 ug/ul | NcoI 20 ul BamHI 20 ul | NcoI 20 ul BamHI 20u1 | 0.1 | 500 | #4 |

TABLE 2-continued

| Plasmid | size | plasmid # | WFI | Buffer | BSA | plasmid* | 37 C. cut PM | O/N 37 C. cut AM | Final Conc (ug/ul) | Final Vol (ul) | ID |
|---|---|---|---|---|---|---|---|---|---|---|---|
| | | | | Repeat Linearize Vectors for Cloning | | 50 ug in 1 ml | | | after Qiagen PCR clean kit | | |
| pXIC-nHis | 3180 bp | p0042 | 350 ul | 100 ul BamHI buffer | 10 ul | 500 ul 0.1 ug/ul | BamHI 20 ul | BamHI 20 ul | 0.1 | 500 | #5 |
| pXIC-cHA | 3271 bp | p0043 | 310 ul | 100 ul BamHI buffer | 10 ul | 500 ul 0.1 ug/ul | NcoI 20 ul BamHI 20 ul | NcoI 20 ul BamHI 20 ul | 0.1 | 500 | #6 |

Note:
pST 1.66 (mega) ug/ul EcoRI 20 units/ul EcoRI buffer
pST-nHA 1.6 ug/ul (mega) NheI 10 units/ul Buffer 2
pST-cHA 1.71 (mega) ug/ul BamHI 20 units/ul BamHI buffer
pXIC 1.18 (mega) ug/ul NcoI 10 units/ul Buffer 4
pXIC-nHis 0.71 (maxi) ug/ul XhoI 20 units/ul Buffer 2
pXIC-cHA 0.3 ug/ul (maxi)
*all plasmids had been cut once, filled-in and cleaned before
Verify the cut completion by gel (load 5 ul, i.e. 0.25 ug)
Store the cut plasmid at −20 C. or proceed to next step.
(2) Clean
Clean the cut plasmid using Qiagen PCR cleaning kit   (10 ug/kit, 5 kits per plasmid)
Elute with 100 ul WFI per kit.
Combine all 5 kits (~500 ul, ~0.1 mg/ml).
Run gel (load 2.5 ul, ~0.25 ug) to verify DNA conc.

A PCR fragment encoding CAT was prepared specific for each linearized vector with 5' and 3' ends complementary to the corresponding vector. The PCR fragments were cleaned using Qiagen PCR cleaning kit and eluted with 30 μl ½ TE for each product. Ten μl was used for each clone reaction. The following steps were performed to introduce the linearized vector and corresponding PCR fragment into a host cell:

Prechill Eppendorf tubes
Add 10 μl CAT PCR fragment (Qiagen cleaned)
Add 1 μl appropriate linear vector (0.05 ug)
Add 10 μl chemically competent cells. Tap gently
On ice for 45 min
Heat shock at 42C for 60 sec
Add 100 μl SC to recover
Shake at 225 RPM 37C for 1 hour
Plate entire volume for (pST Clone) or half volume (for pXic Clone)
Incubate Overnight at 37C
Transformation efficiency was checked by phenol gel. The following was performed:
Place 30 μl WFI in each Eppendorf tube
Add 30 μl Phenol/Chloroform/Isoamyl alcohol to the tube
Pick and disperse the colony to each tube. Save the tip.
Load 20 μl top layer to agarose gel (opalescent and cloudy, do not need loading buffer). Also include the blank vector.
Run at ~90 volts for 25 min.
The transformation efficiency after one treatment and two treatments with restriction enzyme is shown below in Tables 3 and 4 for each clone. The data represent the percentage of cells with the vector and proper insert.

TABLE 3

| phCMV Cloning Vector | % transformation after one Treatment | % transformation after two Treatments |
|---|---|---|
| pST | 88% | 89% |
| pST-nHA | 63% | 100% |
| pST-cHA | 89% | 100% |

TABLE 4

| pIX Cloning Vector | % linear vector after one Treatment | % linear vector after two Treatments |
|---|---|---|
| pXIC | 38% | 67% |
| PXIC-nHis | 60% | 75% |
| PST-cHA | 50% | 78% |

Example 9

Clone for In vitro Transcription & Translation—Kit Components

The resulting vectors contain a T7 promoter and they can be used as templated in cell free in vitro transcription & translation systems that utilize T7 RNA polymerase to generate message. The kit can include:

| ITEM | DESCRIPTION | QUANTITY |
|---|---|---|
| PCR Cloning vector | One of the linear Cloning-adapted vectors: pIX/Xi, | 24 μl |

-continued

| ITEM | DESCRIPTION | QUANTITY |
|---|---|---|
| SmartCells ™ Chemically Competent E. coli | pIX2/Xi, or pIX3/Xi. For vector maps, see page 14–16. Chemically competent E. coli provided at 1 × 10$^9$ cfu/μg transformation efficiency. SmartCells ™ Competent E. coli are optimized to clone your PCR fragments efficiently into the cloning vector. F$^-$ recA1 endA1 hsdR17 supE44 thi-1 gyrA96 relA1 φ801acZΔM15 Δ(lacZYA-argF)U169SmartCells ™ Competent E. coli Genotype | 5 × 50 μl |
| Control template | A 700 base pair chloramphenicol acetyl transferase gene fragment provided as a control template for enzymeless, directional PCR cloning | 10 μl (1 ng/μl) |
| Instruction Manual | | |

While particular embodiments of the invention have been described in detail, it will be apparent to those skilled in the art that these embodiments are exemplary rather than limiting, and the true scope of the invention is that defined in the following claims.

What is claimed is:

1. A method for cloning a nucleic acid fragment into a vector comprising, flanking the fragment with first and second flanking homology sequences, and contacting the fragment with a linearized vector having sequences homologous to the first and second flanking homology sequences under conditions such that the nucleic acid fragment is incorporated into the vector by recombination in a host cell, wherein the ratio of vector and fragment to host cell is about 20 fg to about 100 fg vector and fragment per host cell.

2. The method of claim 1, wherein the first and second flanking homology sequences are incorporated to the nucleic acid fragment by PCR.

3. The method of claim 2, wherein the resulting nucleic acid fragment is a transcriptionally active PCR fragment.

4. The method of claim 1, wherein said first and second flanking homology sequences further comprise a functional element.

5. The method of claim 4, wherein the functional element is selected from the group consisting of a promoter, a terminator, a nucleic acid fragment encoding a selection marker gene, a nucleic acid fragment encoding a protein, encoding a fusion tag, a nucleic acid fragment encoding a portion of a selection marker gene, a nucleic acid fragment encoding a growth promoting protein, a nucleic acid fragment encoding a transcription factor, and a nucleic acid fragment encoding an autofluorescent protein (e.g. GFP), and a nucleic acid fragment encoding a peptide.

6. The method of claim 1, wherein the nucleic acid fragment comprises an additional element.

7. The method of claim 6, wherein the additional element is selected from the group consisting of an operably linked promoter, a termination sequence, an operon, a fusion tag, a signal peptide for intracellular or intercellular trafficking, a peptide, a protein, an antisense sequence, a ribozyme, and a protein binding site.

8. The method of claim 5, wherein the fusion tag is selected from the group consisting of 6× to 10× his-tag, GST tag, fluorescent protein tag, Flag tag, and HA tag.

9. The method of claim 7, wherein the protein comprises enzymes, receptors, antibodies, transcription factors, lymphokines, hormones, a functional motif or domain, and antigens.

10. The method of claim 1, wherein the vector comprises a plasmid, a cosmid, or a bacterial artificial chromosome (BAC).

11. The method of claim 10, wherein the plasmid comprises a functional selection marker.

12. The method of claim 11, wherein the plasmid is maintained in the host cell under the selection condition selecting for the functional selection marker.

13. The method of claim 1, wherein the vector comprises a dysfunctional selection marker that lacks a critical element, and wherein the critical element is supplied by said nucleic acid fragment upon successful recombination.

14. The method of claim 13, wherein the dysfunctional selection marker is a reporter gene.

15. The method of claim 1, wherein the vector comprises a negative selection element detrimental to host cell growth, and wherein the negative selection element is disabled by said nucleic acid fragment upon successful recombination.

16. The method of claim 15, wherein the negative selection element is inducible.

17. The method of claim 1, wherein the vector comprises a dysfunctional selection marker and a negative selection element.

18. The method of claim 1, wherein the host cell is a bacterium.

19. The method of claim 18, wherein the bacterium is capable of in vivo recombination.

20. The method of claim 18, wherein the bacterium is selected from the group consisting of JC8679, TB1, DH5α, DH5, HB101, JM101, JM109, and LE392.

21. The method of claim 1, wherein said first and second flanking homology sequences are at least 11 bp.

22. The method of claim 1, wherein said first and second flanking homology sequences are at least 25 bp.

23. The method of claim 1, wherein said first and second flanking homology sequences are at least 35 bp.

24. The method of claim 1, wherein said first and second flanking homology sequences are at least 45 bp.

25. The method of claim 1, wherein said first and second flanking homology sequences are greater than 60 bp.

26. The method of claim 1, wherein the contacting comprises transforming a host cell with the vector and the nucleic acid fragment.

27. The method of claim 26, wherein the transformation comprises chemical transformation.

28. The method of claim 1, wherein the host cell comprises a cell bearing the vector.

29. The method of claim 28, wherein the contacting comprises transforming the host cell bearing the vector with the nucleic acid fragment.

30. The method of claim 1, wherein at least one of said cell, said nucleic acid fragment and said vector are present at an amount of about $2 \times 10^7$, 0.4–2.0 µg, and 0.05–0.1 µg respectively.

31. The method of claim 1, wherein said vector is prepared by the digestion of a vector and purification of digested vector.

32. The method of claim 1, wherein the recombination comprises homologous recombination.

33. The method of claim 1, wherein at least 85% of the cells have undergone successful recombination.

34. The method of claim 1, wherein 100% of the cells have undergone successful recombination.

35. The method of claim 1, wherein at least 90% of the cells have undergone successful recombination.

36. The method of claim 1, wherein at least 95% of the cells have undergone successful recombination.

37. A method for selecting for successful transformation of a vector by a nucleic acid insert comprising:
providing a nucleic acid insert flanked by first and second flanking homology sequences that is adapted for recombining with homologous sequences in a vector, and wherein the vector has a dysfunctional selection marker lacking a critical element and said nucleic acid insert contains said critical element;
contacting the nucleic acid insert with the vector to effect recombination at homologous sites such that the said critical element is supplied to the vector by the nucleic acid insert and said dysfunctional selection marker is restored to a functional one; and,
selecting the successfully restored selection marker based upon growth of a host containing the successfully recombined vector that allows the host to grow or be identified in a selective environment.

38. The method of claim 37, wherein the recombining is by homologous recombination.

39. A method for selecting for successful transformation of a vector by a nucleic acid insert comprising:
providing a nucleic acid insert flanked by first and second flanking homology sequences that is adapted for recombining with homologous sequences in a vector, and wherein the vector includes a negative selection element detrimental to cell growth;
contacting the nucleic acid insert with the vector to effect recombination at homologous sites such that said negative selection element is disabled; and,
selecting for successful transformation based on the absence of a functional negative selection element.

40. The method of claim 39, wherein the negative selection element is inducible.

41. The method of claim 39, wherein the selection step comprises inducing the negative selection element.

42. The method of claim 39, wherein the negative selection element is disabled by insertion of a sequence encoding a selection marker.

43. A method of generating a substantially background-free linearized vector preparation, comprising:
providing a circular vector comprising a restriction enzyme cleavage site, wherein said site is flanked by homologous sequences;
linearizing said vector with a restriction enzyme; and
purifying said linearized vector to a purity of at least about full length vector.

44. The method of claim 43, wherein said purification comprises chromatography.

45. The method of claim 44, wherein said chromatography comprises affinity chromatography.

46. The method of claim 45, wherein said affinity chromatography comprises capturing an undigested vector, said undigested vector comprising binding molecule in a cloning site such that said binding molecule is not present on the linearized vector due to cleavage by at least one restriction enzyme.

47. The method of claim 46, wherein the binding molecule comprises a PNA binding sequence.

48. The method of claim 45, wherein said affinity chromatography comprises capturing only the linearized vector, said linearized vector comprising a binding site.

49. The method of claim 48, wherein said binding site comprises an end of the vector that is exposed by the restriction enzyme cleavage, wherein said end is captured by a complementary probe on the affinity column.

50. The method of claim 43, wherein said purification comprises PCR amplification of said linearized vector.

51. The method of claim 43, wherein said purification comprises PCR amplification of said linearized vector and chromatography purification.

52. The method of claim 43, wherein said purification results in at least about 100% linearized vector composition.

53. The method of claim 43, wherein said purification results in at least about 99% linearized vector composition.

54. The method of claim 43, wherein said purification results in at least about 98% linearized vector composition.

55. A method of introducing more than one nucleic acid fragment into a vector within a cell, comprising:

providing a first nucleic acid fragment comprising a first coding sequence flanked by a first and a second homologous sequence, wherein said first and second homologous sequences are added to the first coding sequence by PCR;

providing a second nucleic acid fragment comprising a second coding sequence flanked by a third and a fourth homologous sequence, wherein said third and fourth homologous sequences are added to the second coding sequence by PCR;

providing a linearized vector comprising a first end and a second end, wherein said first and second ends are respectively homologous to said first homologous sequence on said first nucleic acid fragment and to said third homologous sequence on said second nucleic acid fragment; and introducing said nucleic acid fragments and said linearized vector into the cell under conditions such that said nucleic acid fragments are incorporated into said vector by recombination in the cell.

56. The method of claim 55, further comprising culturing said recombinant cell.

57. The method of claim 55, further comprising selecting a cell that has undergone successful recombination.

58. The method of claim 57, wherein the selecting comprises growing said cell under selective conditions.

59. The method of claim 58, wherein at least 80% of the cells have undergone successful recombination.

60. The method of claim 58, wherein at least 90% of the cells have undergone successful recombination.

61. The method of claim 58, wherein 100% of the cultured cells have undergone successful recombination.

62. The method of claim 55, wherein said linearized vector is prepared by the digestion of a vector and purification of digested vector.

63. The method of claim 55, wherein said first or said second homologous sequence comprises at least about 25 bases.

64. The method of claim 55, wherein said introducing step comprises chemical insertion of said nucleic acid fragments and said linearized vector into said cell.

65. The method of claim 56, wherein said cell, said nucleic acid fragments and said linearized vector are present at an amount of about $2 \times 10^7$, 0.4–2.0 µg, and 0.05–0.1 µg respectively.

66. A system for cloning more than one nucleic acid fragment into a vector without at least one of a restriction enzyme, a ligase, a gyrase, or a single stranded DNA binding protein, the system comprising more than one nucleic acid fragment each flanked by first and second adapter sequences, and a vector having sequences homologous to the most 5' and most 3' adapter sequences, wherein the one or more nucleic acid fragment is adapted to incorporate into the vector by recombination.

67. A method for generating a plurality of recombinant constructs, comprising the steps of:

introducing into a host organism a linearized polynucleotide vector and a linearized polynucleotide vector insert, wherein the insert and the vector have respective regions of homology at ends thereof, under conditions favoring assembly of the vector and the insert into a circular recombinant construct in the host organism, such that such assembly occurs in at least 95% of the host organisms;

repeating the introducing step with the same or different vector and a different vector insert a plurality of times to produce a plurality of host organisms containing different recombinant constructs; and creating a collection of such host organisms by replicating the host organisms without a selection step.

68. The method of claim 67, wherein said linearized polynucleotide vector insert comprise functional element.

69. The method of claim 68, wherein the functional element is selected from the group consisting of a promoter, a terminator, a nucleic acid fragment encoding a selection marker gene, a nucleic acid fragment encoding a protein, encoding a fusion tag, a nucleic acid fragment encoding a portion of a selection marker gene, a nucleic acid fragment encoding a growth promoting protein, a nucleic acid fragment encoding a transcription factor, and a nucleic acid fragment encoding an autofluorescent protein (e.g. GFP), and a nucleic acid fragment encoding a peptide.

70. The method of claim 69, wherein the fusion tag is selected from the group consisting of 6× to 10× his-tag, GST tag, fluorescent protein tag, Flag tag, and tag.

71. The method of claim 67, wherein the linearized polynucleotide vector insert comprises an additional element selected from the group consisting of operably linked promoter, a termination sequence, an operon, a fusion tag, a signal peptide for intracellular or intercellular trafficking, a peptide, a protein, an antisense sequence, a ribozyme, and a protein binding site.

72. The method of claim 71, wherein the protein comprises enzymes, receptors, antibodies, transcription factors, lymphokines, hormones, a functional motif or domain, and antigens.

73. The method of claim 67, wherein the vector comprises a plasmid, a cosmid, or a bacterial artificial chromosome (BAC).

74. The method of claim 1, wherein the host organism is a bacterium.

75. The method of claim 73, wherein the bacterium is capable of in vivo recombination.

76. The method of claim 74, wherein the bacterium is selected from the group consisting of JC8679, TB1, DH5α, DH5, HB101, JM109, JM109, and LE392.

77. The method of claim 67, wherein said linearized vector insert comprises first and second flanking homology sequences of 11 bp.

78. The method of claim 67, wherein said linearized vector insert comprises first and second flanking homology sequences of up to 25 bp.

79. The method of claim 67, wherein said linearized vector insert comprises first and second flanking homology sequences of up to 35 bp.

80. The method of claim 67, wherein said linearized vector insert comprises first and second flanking homology sequences of greater than 60 bp.

81. The method of claim 67, wherein the introducing comprises transforming a host cell with the vector and the vector insert.

82. The method of claim 81, wherein the transformation comprises chemical transformation.

83. The method of claim 67, wherein at least one of said host organism, said vector insert and said vector are present at an amount of about $2 \times 10^7$, 0.4–2.0 µg, and 0.05–0.1 µg respectively.

84. The method of claim 67, wherein said linearized vector is prepared by the digestion of a vector and purification of digested vector.

85. The method of claim 67, wherein assembly occurs in 99% of the organisms.

86. The method of claim 39, further comprising the method of claim 51.

* * * * *

UNITED STATES PATENT AND TRADEMARK OFFICE
CERTIFICATE OF CORRECTION

PATENT NO. : 6,936,470 B2
DATED : August 30, 2005
INVENTOR(S) : Liang et al.

It is certified that error appears in the above-identified patent and that said Letters Patent is hereby corrected as shown below:

<u>Title page,</u>
Item [63], Related U.S. Application Data, should read as follows:
-- This application is a continuation-in-part of U.S. Application No. 09/836,436, filed on April 17, 2001, entitled "FAST AND ENZYMELESS CLONING OF NUCLEIC ACID FRAGMENTS", which is hereby incorporated herein by reference in its entirety. --.

<u>Column 28,</u>
Lines 36-37, insert -- 80% -- between "about" and "full".

Signed and Sealed this

Fourth Day of April, 2006

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 46
<212> TYPE: DNA
<213> ORGANISM: Artificial Sequence
<220> FEATURE:
<223> OTHER INFORMATION: 5' PCR Primer

<400> SEQUENCE: 1
ctgcaggcac cgtcgtcgac ttaacaatgg agaaaaaaat cactgg          46

<210> SEQ ID NO 2
<211> LENGTH: 46
<212> TYPE: DNA
<213> ORGANISM: Artificial Sequence
<220> FEATURE:
<223> OTHER INFORMATION: 3' PCR Primer

<400> SEQUENCE: 2
catcaatgta tcttatcatg tctgattacg ccccgccctg ccactc          46
```